United States Patent
Pauletti et al.

(10) Patent No.: US 6,905,701 B2
(45) Date of Patent: *Jun. 14, 2005

(54) FORMULATIONS FOR TRANSMUCOSAL VAGINAL DELIVERY OF BISPHOSPHONATES

(75) Inventors: Giovanni M. Pauletti, Loveland, OH (US); Chris E. Clendening, Cleves, OH (US)

(73) Assignee: UMD, Inc., Cincinnati, OH (US)

(*) Notice: Subject to any disclaimer, the term of this patent is extended or adjusted under 35 U.S.C. 154(b) by 123 days.

This patent is subject to a terminal disclaimer.

(21) Appl. No.: 10/349,029

(22) Filed: Jan. 22, 2003

(65) Prior Publication Data

US 2004/0005345 A1 Jan. 8, 2004

Related U.S. Application Data

(63) Continuation-in-part of application No. 09/626,025, filed on Jul. 27, 2000, now Pat. No. 6,572,874, which is a continuation-in-part of application No. 09/249,963, filed on Feb. 12, 1999, now Pat. No. 6,086,909, which is a continuation-in-part of application No. 09/079,897, filed on May 15, 1998, now Pat. No. 6,197,327.

(60) Provisional application No. 60/049,325, filed on Jun. 11, 1997, and provisional application No. 60/146,218, filed on Jul. 28, 1999.

(51) Int. Cl.$^7$ ............ A61F 6/06; A61F 13/00; A61F 13/02; A61K 31/66
(52) U.S. Cl. ............ 424/433; 424/431; 424/430; 514/102
(58) Field of Search ............ 424/423, 430, 424/431, 433; 514/102, 54, 57, 89

(56) References Cited

U.S. PATENT DOCUMENTS 6,572,874 B1 * 6/2003 Harrison et al. ............ 424/430

* cited by examiner

Primary Examiner—Thurman K. Page
Assistant Examiner—Blessing Fubara
(74) Attorney, Agent, or Firm—Hana Verny

(57) ABSTRACT

Devices, methods, and improved formulation for transmucosal vaginal delivery of bisphosphonates. A targeted site delivery of bisphosphonates to the systemic circulation using a vaginal device comprising an improved bisphosphonate formulation for transmucosal delivery. A method for treatment of osteoporosis and related bone and skeleton diseases, for prevention of bone breakdown and loss of bone mass and strength by intravaginal administration of bisphosphonates to the vagina and transmucosal delivery of bisphosphonates to the general circulation.

27 Claims, 5 Drawing Sheets

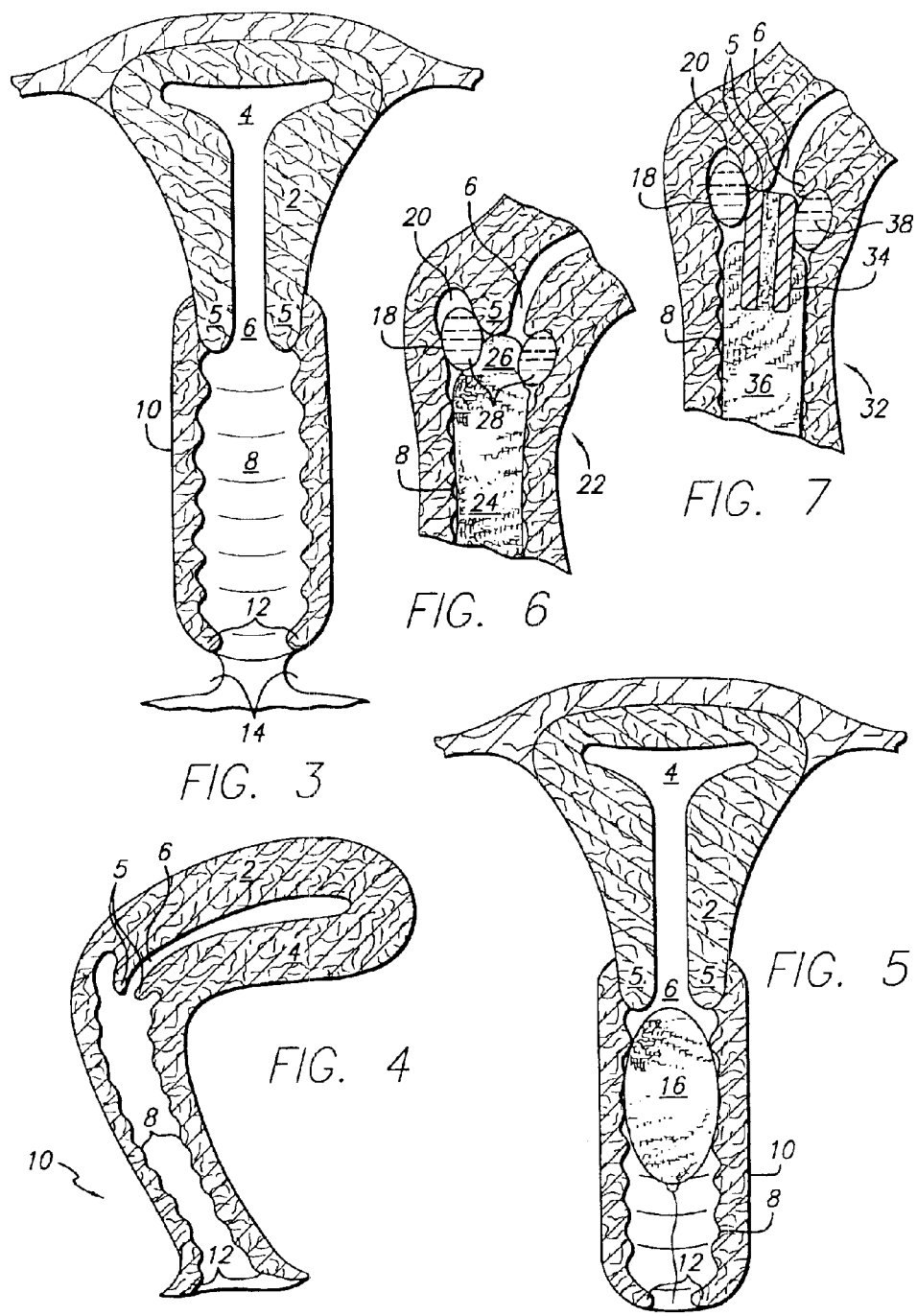

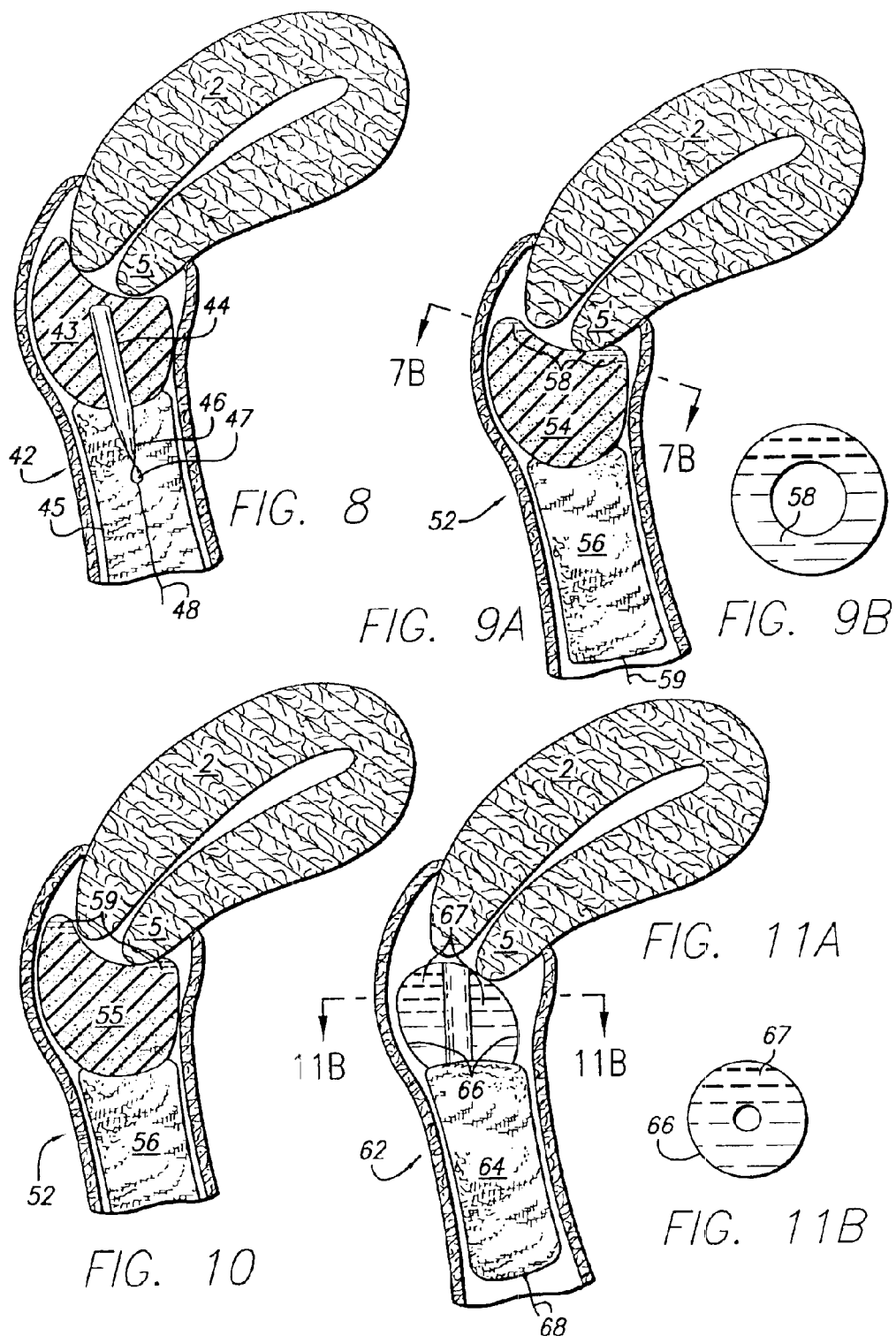

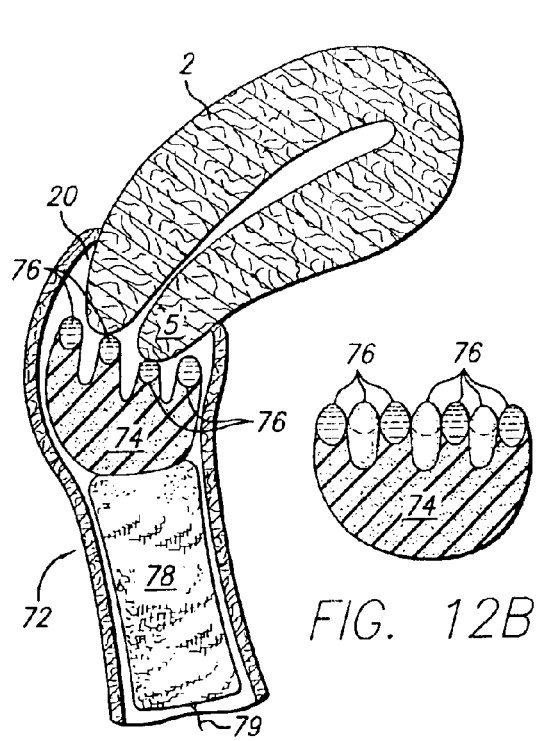
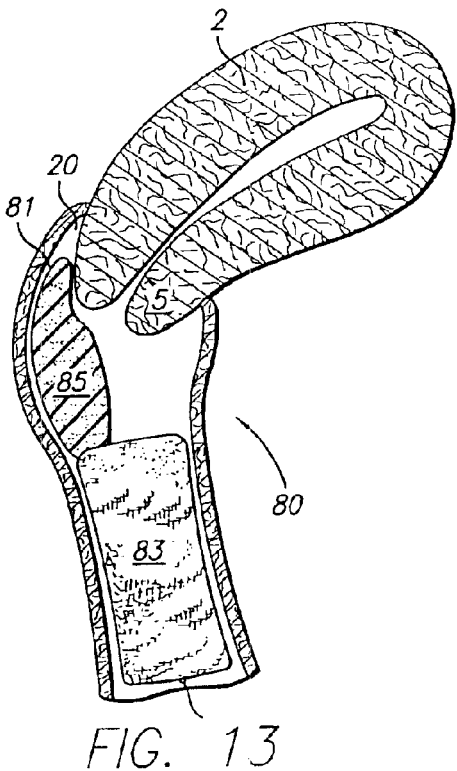
FIG. 12A  FIG. 12B  FIG. 13
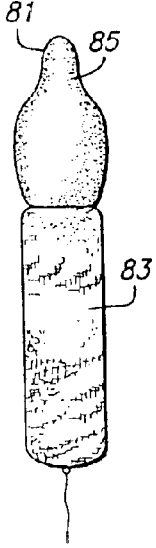
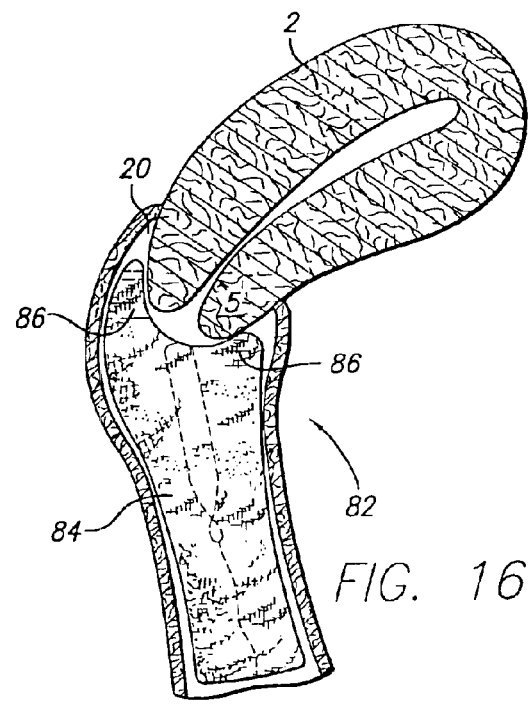
FIG. 14  FIG. 15  FIG. 16

FORMULATIONS FOR TRANSMUCOSAL VAGINAL DELIVERY OF BISPHOSPHONATES

This application is a continuation-in-part of U.S. patent application Ser. No. 09/626,025, filed Jul. 27, 2000 now U.S. Pat. No. 6,572,874 which is a continuation-in-part of U.S. patent application Ser. No. 09/249,963, filed Feb. 12, 1999, issued as U.S. Pat. No. 6,086,909, which is a continuation-in-part of the U.S. patent application Ser. No. 09/079,897, filed on May 15, 1998, issued as U.S. Pat. No. 6,197,327, which claims priority of the Provisional Application Ser. No. 60/049,325, filed Jun. 11,1997, under 35 U.S.C. §111(b). This application is based on and claims also priority of the Provisional Application Ser. No. 60/146,218 filed on Jul. 28, 1999.

BACKGROUND OF THE INVENTION

1. Field of the Invention

The present invention concerns improved formulations for transmucosal vaginal delivery of bisphosphonates. In particular, the invention concerns an improved formulation comprising from about 0.01 to about 3200 mg of a selected bisphosphonate, from about 0.01 to about 5% of hydroxypropyl methylcellulose, from about 40 to about 95% of a saturated monoglyceride, diglyceride or triglyceride of fatty acids of length from 8 to 18 carbons or a mixture thereof, from about 5 to about 25% of ethoxydiglycol and, optionally, other pharmaceutically acceptable excipients and additives. The improved transmucosal vaginal formulation delivers more than 60 times more bisphosphonates than can be delivered orally.

The invention further concerns transmucosal devices incorporated with the improved transmucosal vaginal bisphosphonate formulation suitable for use in a method for treatment of osteoporosis, Paget's disease, nonmetastatic neoplastic disease, metastatic cancer of bone, and other related diseases of bone and skeleton and for prevention of bone breakdown, loss of bone mass and strength. The method for treatment of said diseases comprises a step of delivering the improved transmucosal vaginal formulation to the vagina for delivery of bisphosphonates to the systemic circulation.

2. Background and Related Art

Osteoporosis and therewith associated loss of bone mass and strength leading to bone breakdown and fractures is a major medical problem in postmenopausal women.

A number of approaches for prevention of osteoporosis in this patient group have been proposed. These approaches include the administration of high doses of calcium and vitamin D in conjunction with the administration of estrogens, as well as the administration of synthetic substances which bind to estrogen receptors such as raloxifen, tamoxifen, etc.

One of the newer investigated approaches for prevention of osteoporosis is the administration of bisphosphonates. Bisphosphonates were found to prevent bone resorption leading to reduction of bone fractures, especially the fractures of spine and hip. Recent studies have demonstrated that these compounds prevent the loss of bone and enhance bone density in the postmenopausal female population and in patients with Paget's disease of bone (*Journal of Clinical Endocrinology and Metabolism,* 82(1):265–274 (1997); *Journal of Bone and Mineral Research,* 12(10):1700–1707 (1997); *American Journal of Medicine,* 106(5):513–520 (1997); *Journal of Clinical Endocrinology and Metabolism,* 83(2):396–402 (1998)).

Cumulatively, the above references show that bisphosphonates prevent a breakdown of bone, strengthen bone, increase a bone mass and markedly reduce fractures.

The bisphosphonates were additionally investigated for treatment of cancer, as described, for example, in *New England Journal of Medicine,* 335:1785–1791 (1996) which reports a decreased frequency of skeletal events in patients with multiple myeloma involving bone and breast cancer with osteolytic metastases following a treatment with bisphosphonates. Clinical trials described in *New England Journal of Medicine,* 339:398–400 (1998) have shown that adjunctive treatment with bisphosphonates reduces the incidence and number of new bone and visceral metastases in women with high risk, primary breast cancer.

Numerous bisphosphonates are now available for therapeutical use, however, their administration and delivery remains problematic.

A most preferred mode of drug delivery for any drug is, of course, the oral administration. However, this mode of administration of bisphosphonates is limited by the low gastrointestinal absorption and by overall low gastrointestinal tolerability of bisphoshonates. Gastrointestinal absorption of the bisphosphonates is very poor and, typically, only about 1% or less of the administered dose is absorbed into the general circulation.

Additionally, a significant number of women treated with oral bisphosphonates were reported to develop irritation of esophageal mucosa, esophageal reflux and esophagitis (*Digestive Diseases and Sciences,* 43 (9):1998–2002 (1998); *Digestive Diseases and Sciences,* 43(5):1009–1015 (1998)). To lessen these undesirable adverse reactions, the oral administration of bisphosphonates requires a very strict regimen which is hard to follow. A noncompliance with this regimen leads to a failure of the treatment.

A primary problem connected with oral administration of bisphosphonates, however, is the inefficiency of the oral delivery because only less than 1% of bisphosphonates is absorbed following the oral administration (*Drugs,* 53(3):415–434 (1997).

In view of the problems encountered with oral administration of bisphosphonates which limits their utility, it is clear that new delivery mechanisms which would enhance the absorption and bioavailability of these drugs and yet avoid a need for intravenous administration would be extremely advantageous for achieving and increasing a therapeutic potential of bisphosphonates.

U.S. patent application Ser. No. 09/626,025, filed on Jul. 27, 2000, allowed, describes a transmucosal vaginal composition which improves delivery of bisphosphonates by 10 to 30 times compared to the oral delivery. However, the efficacy of that composition is still rather low and thus any further improvement in the efficacy of the bisphosphonate delivery would be an important practical and economic achievement.

It is, therefore, an objective of the present invention to provide an improved formulation for transmucosal vaginal delivery of bisphosphonates suitable to be administered directly to the vagina or incorporated into an appropriate vaginal device as well as methods using such formulation for treatment of osteoporosis, Paget's disease and other related diseases of bone and skeleton or for treating and prevention of cancer, which formulation would enable delivery of larger amounts of bisphosphonates to the general circulation than those delivered orally or with prior formulations.

All references, patents and patent applications cited herein are hereby incorporated by reference in their entirety.

SUMMARY OF THE INVENTION

One aspect of the present invention is an improved transmucosal vaginal formulation for delivery of larger amounts of bisphosphonates transmucosally through the vaginal mucosa to a systemic circulation.

Another aspect of the present invention is an improved transmucosal vaginal formulation comprising an appropriate amount of a selected bisphosphonate in admixture with from about 0.01 to about 5% of hydroxypropyl methylcellulose, from about 40 to about 95% of a saturated monoglyceride, diglyceride or triglyceride of fatty acids of length from 8 to 18 carbons or a mixture thereof, from about 5 to about 25% of ethoxydiglycol and, optionally, with other pharmaceutically acceptable excipients and additives.

Another aspect of the present invention is an improved transmucosal vaginal formulation suitable for incorporation into a vaginal device for transmucosal delivery of bisphosphonates into the systemic circulation for treatment of osteoporosis, Paget's disease and other related diseases of bone and skeleton or metastatic or nonmetastatic neoplastic disease.

Another aspect of this invention is an improved transmucosal vaginal formulation for delivery of bisphosphonates into the systemic circulation, said formulation comprising a bisphosphonate selected from the group consisting of alendronate, clodronate, etidronate, pamidronate, tiludronate, ibandronate, zoledronic acid, olpadronate, risedronate, neridronate, incadronate and minodronate formulated for effective transmucosal absorption, said formulation useful for prevention and treatment of osteoporosis, Paget's disease, other diseases of bone and skeleton and cancer.

Still yet another aspect of this invention is an improved transmucosal vaginal formulation comprising a bisphosphonate selected from the group consisting of alendronate, clodronate, etidronate, pamidronate, tiludronate, ibandronate, zoledronic, olpadronate, risedronate, neridronate, incadronate and minodronate in dosage unit form, for delivery to a vagina for treatment and/or prevention of osteoporosis, Paget's disease, other diseases of bone and skeleton or cancer, wherein said formulation comprises a combination of an effective amount of a bisphosphonate with from about 0.01 to about 5% of hydroxypropyl methylcellulose, from about 40 to about 95% of a saturated monoglyceride, diglyceride or triglyceride of fatty acids of length from 8 to 18 carbons, or a mixture thereof, from about 5 to about 25% of ethoxydiglycol, wherein said formulation is prepared as a vaginal suppository, tablet, bioadhesive tablet, capsule, microparticle, bioadhesive microparticle, cream, lotion, foam, film, ointment, solution, gel, or a sustained release gel, tablet or capsule, or a sustained release suppository administered to the vagina or incorporated into a device of the invention.

Still another aspect of this invention is a vaginal device, such as a tampon, tampon-like device, pessary, ring, sponge, strip or cup incorporated with an improved transmucosal vaginal formulation comprising a bisphosphonate selected from the group consisting of alendronate, clodronate, etidronate, pamidronate, tiludronate, ibandronate, zoledronic acid, olpadronate, risedronate, incadronate, minodronate and neridronate, suitable for transmucosal absorption through a vaginal mucosa for delivery of bisphosphonates to the systemic circulation.

Yet another aspect of this invention is a vaginal device incorporated with the improved transmucosal vaginal formulation of the invention suitable for delivering an effective amount of a bisphosphonate to the systemic circulation for treatment of osteoporosis, Paget's disease, metastatic or nonmetastatic cancer of bone, other bone or skeleton diseases or cancer and prevention of development of osteoporosis, wherein said device is a vaginal ring, vaginal strip, vaginal tampon, vaginal applicator, absorbent vaginal tampon, vaginal pessary, vaginal capsule, or vaginal suppository or tampon or tampon-like device comprising a vaginal suppository.

Still yet another aspect of this invention is a method for treating a female patient suffering from, or being at risk of developing osteoporosis, Paget's disease, metastatic cancer of bone or other disease of bone or skeleton or cancer, said method comprising a step of contacting the vaginal mucosa with an improved formulation comprising a therapeutically effective amount of a bisphosphonate selected from the group consisting of alendronate, clodronate, etidronate, pamidronate, tiludronate, ibandronate, zoledronic acid, olpadronate, risedronate, incadronate, minodronate and neridronate in admixture with from about 0.01 to about 5% of hydroxypropyl methylcellulose, from about 40 to about 95% of a saturated monoglyceride, diglyceride or triglyceride of fatty acids of length from 8 to 18 carbons, or a mixture thereof, from about 5 to about 25% of ethoxydiglycol, and, optionally, with pharmaceutically acceptable excipients and additives, wherein said bisphosphonate is present in said formulation in an amount sufficient to attain a therapeutically effective amount of the bisphosphonate in a patient's plasma.

Another aspect of this invention is a method for preparation of a transmucosal medicated device comprising manufacturing said device comprising an improved transmucosal vaginal bisphosphonate formulation or incorporating said device with said improved formulation for transmucosal vaginal delivery of said bisphosphonate, wherein said device is a vaginal tampon, a vaginal applicator, a vaginal strip, a vaginal capsule or a container comprising tampon or a tampon-like device, or a vaginal strip, vaginal cup, vaginal ring, vaginal pessary, vaginal tablet, vaginal suppository, vaginal sponge, bioadhesive tablet, microparticle or bioadhesive microparticle, and wherein said formulation is prepared and incorporated into said device as a cream, lotion, foam, ointment, solution or gel.

BRIEF DESCRIPTION OF THE DRAWINGS

FIG. 3 is a cross-sectional representation of a portion of the female reproductive organs including the uterus and vagina in the upright orientation.

FIG. 4 is a cross-sectional side view representation of a portion of the female reproductive organs including the uterus and vagina.

FIG. 5 is the representation of FIG. 2 showing placement of a vaginal suppository incorporated with an improved formulation of the invention for a drug delivery according to the present invention.

FIG. 6 is a cross-sectional side view representation of the vaginal area adjacent the cervix showing placement of a tampon incorporated with bisphosphonate formulation.

FIG. 7 is the representation of FIG. 3 showing placement of a tampon for bisphosphonate delivery according to the present invention.

FIG. 8 is the representation of FIG. 3 showing placement of a tampon for drug delivery incorporating a distal porous foam section.

FIG. 9A is the representation of FIG. 4 showing placement of a tampon for drug delivery incorporating a distal porous foam cup. FIG. 9B is a cross-sectional view of the embodiment shown in FIG. 9A, taken in the direction indicated by the arrows labeled 9B in FIG. 9A.

FIG. 10 is an alternative embodiment to one shown in FIG. 8A in which an improved bisphosphonate formulation is contained in the entire porous foam cup.

FIG. 11A is the representation of FIG. 4 showing placement of a tampon for drug delivery incorporating a distally placed suppository or gel capsule containing an improved formulation. FIG. 11B is a cross-sectional view of the embodiment shown in FIG. 11A, taken in the direction indicated by the arrows labeled 11B in FIG. 11A.

FIG. 12A is the representation of FIG. 4 showing placement of a tampon for drug delivery incorporating a distal foam cup comprising "fingers" for cervix enclosure. FIG. 12B is a side view of the distal porous foam cup.

FIG. 13 is the representation of FIG. 4 showing placement of a tampon for delivery of bisphosphonates incorporating a scoop-shaped distal porous foam section.

FIG. 14 is a side view of the embodiment shown in FIG. 13.

FIG. 15 is a front view of the embodiment shown in FIG. 13.

FIG. 16 is the representation of FIG. 4 showing placement of a tampon for drug delivery incorporating distal fibers containing an improved bisphosphonate drug formulation.

DEFINITIONS

Figure 1:
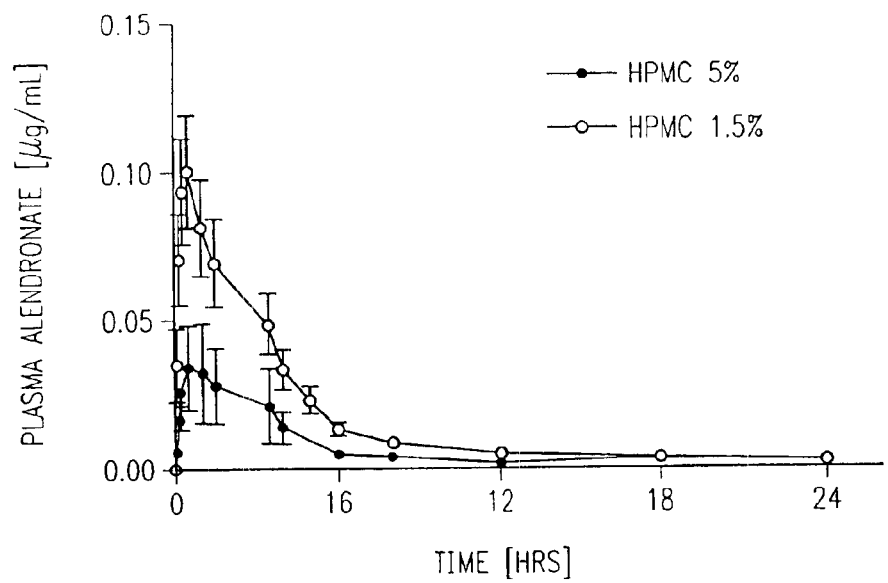
FIG. 1 illustrates concentrations-time profiles of alendronate in plasma ($\mu$g/ml) following vaginal administration of a vaginal suppository consisting of a single dose of alendronate in a prior formulation (5% HPMC) and an improved formulation (1.5% HPMC) to female white New Zealand rabbit.

As described herein:

"Agent", "drug", "compound", "olpadronate", "incadronate" or "minodronate" means a bisphosphonate selected from the group consisting of alendronate, clodronate, etidronate, pamidronate, tiludronate, zoledronic acid, ibandronate, risedronate, neridronate, incadronate, minodronate and any other bisphosphonate known now, or which will become known in the future which has the same properties as bisphosphonates disclosed herein.

"BMD" means bone mineral density.

"HPMC" means hydroxypropyl methylcellulose.

"Saturated monoglyceride, diglyceride or triglyceride of fatty acids of length from 8 to 18 carbons" means a lipophilic carrier as, for example, commercially available, for example, from GattefosséCorp., Saint Priest, Cedex, France, under a trade name SUPPOCIRE®. SUPPOCIRE, such as, for example, SUPPOCIRE AS2X, is chemically defined as semi-synthetic glyceride made of saturated C8–C18 fatty acid glycerides with polyoxyethylenated fatty esters.

"Particulate delivery systems" means particles ranging from nano- to millimeter size that are prepared from natural and/or synthetic polymers and control the delivery of drugs various mechanisms, including dissolution, diffusion, erosion and any combination thereof. Examples, not limiting the scope of these delivery systems, are microparticles, microcapsules, nanoparticles, naospheres, and liposomes.

"Ethoxydiglycol" means a sorption promoter or penetration enhancer commercially available, for example, from Gattefossé Corp., under a trade name TRANSCUTOL®.

DETAILED DESCRIPTION OF THE INVENTION

This invention relates generally to an improved formulations for transmucosal delivery and administration of bisphosphonates through a vaginal mucosa into the systemic circulation. The improved formulation is delivered by administration of the improved bisphosphonate containing transmucosal formulation into a vagina and by subsequent absorption of the bisphosphonate into the systemic blood circulation. The improved formulation achieves a substantial increase in bioavailability of the bisphosphonates in serum. The transmucosal vaginal delivery of bisphosphonates using the improved formulation of the invention increases bioavailability of bisphosphonates in plasma to over 67% compared to the average bioavailability of bisphosphonates in plasma determined after oral delivery and improves the bioavailability by more than 100% compared to a transmucosal formulation previously described in the patent application Ser. No. 09/626,025, allowed, hereby incorporated by reference.

The invention thus concerns finding that a lower concentration of hydroxypropyl methylcellulose, namely a concentration from about 0.01% and up to maximum of 5%, preferably about from 0.5% to about 3%, most preferably about 1.5%, substantially improves a transmucosal absorption of bisphosphonate through the vaginal mucosa. Compared to a previously described formulation comprising from 5% to 25% of hydroxypropyl methylcellulose, the bioavailability of the bisphosphonate in serum following the administration of the improved formulation has more then doubled.

The improved formulation of the invention thus enables delivery of higher concentrations of bisphosphonates and is better suited for treatment of osteoporosis, Paget's disease and other bone and skeleton related diseases without occurrence of undesirable adverse side effects. Treatments of these diseases with the bisphosphonates are currently limited due to the side effects of these drugs which complicate their administration to the patient through oral routes and due to their poor absorption through the gastrointestinal tract. Although these drugs may be administered intravenously, such administration is not convenient as it requires visit to the hospital or to the doctor's office and is considered invasive.

The invention is based on inventors prior discovery that certain pharmaceutical agents, including bisphosphonates, may be conveniently and efficaciously delivered transmucosally to the uterus and/or to the systemic blood circulation and particularly that bisphosphonates may be delivered via this route in substantially increased amounts.

Transmucosal vaginal delivery according to the invention comprises contacting the vaginal mucosa with an improved formulation comprising a selected bisphosphonate in admixture with a lipophilic carrier, mucoadhesive agent, sorption promoter or penetration enhancer. The improved formulation of the invention comprises from about 0.01 to about 3200 mg of a selected bisphosphonate, from about 0.01 to about 5% of hydroxypropyl methylcellulose, from about 40 to about 95% of a saturated monoglyceride, diglyceride or triglyceride of fatty acids of length from 8 to 18 carbons or a mixture thereof, from about 5 to about 25% of ethoxydiglycol and, optionally, other pharmaceutically acceptable excipients and additives.

The preferred formulation of the invention comprises from about 0.01 to about 3200 mg of a selected bisphosphonate, from about 1% to about 3% of hydroxypropyl methylcellulose, from about 60 to about 70% of a saturated monoglyceride, diglyceride or triglyceride of fatty acids of length from 8 to 18 carbons or a mixture thereof, from about 10 to about 20% of ethoxydiglycol and, optionally, other pharmaceutically acceptable excipients and additives.

The most preferred formulation of the invention comprises from about 0.06 to about 0.6 mg of a selected bisphosphonate, about 1.5% of hydroxypropyl methylcellulose, about 68.5% of a saturated monoglyceride, diglyceride or triglyceride of fatty acids of length from 8 to 18 carbons or a mixture thereof, about 15% of ethoxydiglycol and, optionally, other pharmaceutically acceptable excipients and additives.

Exemplary formulations of the invention have the following content:

Alendronate (3 mg) formulation:
68.5% SUPPOCIRE® (semi-synthetic glycerides made of saturated of C8–C18 fatty acids of length from 8 to 18 carbons);
15% TRANSCUTOL® (ethoxydiglycol);
1.5% METHOCEL® (hydroxypropyl methyl cellulose);
14.82% WFI (water for injection); and
0.18% alendronate.

Alendronate (1 mg) formulation:
68.5% SUPPOCIRE® (a mixture of triglyceride of fatty acids glycerides with polyoxyethylenated fatty esters);
15% TRANSCUTOL® (ethoxydiglycol);
1.5% METHOCEL® (hydroxypropyl methyl cellulose);
14.94% WFI (water for injection); and
0.06% alendronate.

Alendronate (10 mg) formulation:
68.5% SUPPOCIRE® (a mixture of triglyceride of fatty acids of length from 8 to 18 carbons);
15% TRANSCUTOL® (ethoxydiglycol);
1.5% METHOCEL® (hydroxypropyl methyl cellulose);
14.41% WFI (water for injection); and
0.59% alendronate.

Transmucosal vaginal delivery is achieved either directly by delivering the formulation of the invention to the vagina or by delivering the formulation of the invention to the vagina incorporated into a vaginal device. The formulation or the device is placed into a close contact with or into a close proximity of the vaginal mucosa wherein the bisphosphonate is either released from the formulation or from the device and either directly or through the action of the mucoadhesive compound and/or penetration enhancer or sorption promoter it comes into a contact with or adheres to the vaginal mucosa where it penetrates the vaginal mucosa and is delivered transmucosally to the systemic blood circulation by being absorbed or transported through vaginal mucosa.

The current invention concerns a specific discovery that the problems encountered during oral delivery of bisphosphonates can be overcome by delivering the bisphosphonates to the blood circulation transmucosally through the vaginal mucosa using an improved transmucosal formulation. Transmucosal delivery of bisphosphonates through vaginal mucosa using said formulation significantly improves systemic bioavailability of bisphoshonates and more than doubles concentrations of bisphosphonates in the plasma compared to a prior transmucosal composition.

Additionally, the invention concerns the discovery that bisphosphonates may be conveniently and efficiently delivered to the systemic circulation using an improved bisphosphonates formulation in the form of suppositories, tablets, capsules, microcapsules, gels, foams, ointments, or creams or using tampons, tampon-like devices, vaginal rings, sponges, strips, cups or pessaries incorporated with said formulation. Any other means for drug delivery suitable for transmucosal vaginal administration are intended to be within the scope of this invention.

I. Vaginal Delivery of Bisphosphonates

The invention thus concerns more efficacious delivery of bisphosphonates into the blood circulation. These compounds are administered into vagina and transferred transmucosally through vaginal mucosa by transmucosal absorption. Transmucosal absorption has been demonstrated for other drugs, as previously described in the above cited patents and patent applications, with direct uptake for many drugs equivalent to intravenous administration.

A vaginal transmucosal approach permits bisphosphonates to be administered as a gel, cream, foam, ointment, tablet, capsule, microcapsule, fluid, powder or suppository formulation either directly or incorporated into the transmucosal device from which the formulation is released, preferably in a sustained time release manner. The bisphosphonate is typically either attached to a lipophilic or hydrophilic carrier, depending on the bisphosphonate charge, and formulated in combination with a mucoadhesive agent to enhance adhesivity of the released compound to the vaginal mucosa and to assure contact with the vaginal mucosa. In order to enhance absorption of the bisphosphonate through the vaginal mucosa, an absorption (sorption) promoter or penetration enhancer for transmucosally administered compounds is utilized as another formulating agent.

Properties of Bisphosphonates

The bisphosphonates constitute a recently developed class of drugs for use in a variety of diseases of bone and calcium metabolism. Up-to-date there are three generations of bisphosphonates.

Bisphosphonates are synthetic analogs of pyrophosphates characterized by phosphorus-carbon-phosphorus backbone that renders them resistant to hydrolysis. The properties of the bisphosphonates vary based on different substitutions at the carbon atom of the phosphorus-carbon-phosphorus backbone.

A group of currently known bisphosphonates include alendronate, clodronate, etidronate, pamidronate, tiludronate, ibandronate, zoledronic acid, olpadronate, risedronate, incadronate, minodronate, and neridronate.

1. Clinical Use of Bisphosphonates

Bisphosphonates are analogues of pyrophosphates and like them, are strongly bound to hydroxyapatite on the bone surface. Biophosphonates are stable and reduce and inhibit activity of osteoclasts, cells functioning in the absorption and removal of osseous tissue.

The clinical use of bisphosphonates is based on their ability to inhibit bone resorption. Thus, the main indications for their use concern diseases with high bone remodeling, such as Paget's disease of bone, osteoporosis, metastatic bone diseases, and malignant and nonmalignant hypercalcemia.

The primary effect of bisphosphonates is the inhibition of bone resorption through cellular mechanisms that effect osteoclast attachment to bone, osteoclast precursor differentiation, and osteoclast survival. The anti-resorptive effect of bisphosphonates is also mediated through effects on the osteoblast.

Bisphosphonates also appear to mediate the anti-cancer effects by modifying the bone surface, altering the bone microenvironment, inhibiting specific enzymatic pathways, and inducing apoptosis in osteoclast and tumor cells. The role of bisphosphonates as anti-cancer agents continues to expand and new and more potent bisphosphonates are continually being introduced into clinical practice.

Doses of bisphosphonates needed to inhibit bone resorption, however, are difficult to achieve orally, due to their poor absorption and potential gastrointestinal irritability. Therefore, their oral use is rather limited.

Despite difficulties encountered with their oral administration, bisphosphonates are very potent drugs when delivered in therapeutic doses. They have a unique spectrum of potency and a mechanism of action. The parent compound, etidronate, was first used in multicentered trials for the treatment of primary osteoporosis and showed success in increasing bone density and controlling fracture rates. The recently approved drug alendronate which is a more potent agent than etidronate, produces a greater increase in bone density, and decreases the number and severity of fractures. Oral and intravenous pamidronate have similar positive effects on bone density. Studies with tiludronate, risedronate, and clodronate show similar effects as therapeutic agents.

2. Adverse Reactions of Orally Administered Bisphosphonates

As discussed above, despite their potential benefits in treating bone disorders, the full therapeutic potential has not been achieved because of severe adverse reactions, lack of efficacy and inconvenient regimen required for bisphosphonate oral administration. The adverse reactions include irritation, ulceration or inflammation of esophagus and stomach. Lack of efficacy is evidenced by poor absorption of bisphosphonates through the intestinal tract resulting in bioavailability of less than 1% of the administered oral dose. The strict regimen required for bisphosphonates oral administration results in great inconvenience for a patient resulting in abandonment of this treatment by many patients.

Until these problems with oral administration will be solved, bisphosphonates will not become drugs of choice for treatment and prevention of osteoporosis and related bone diseases. The current invention provides an alternative method to the oral administration by delivering these drugs transmucosally to the blood in amounts which are more than sixty times higher than those delivered orally.

3. Transmucosal Delivery of Bishoshonates

The transmucosal method eliminates the local gastrointestinal irritation and subsequent ulceration of esophagus and stomach, it is much more efficacious than the oral administration and does not involve dietary or time restrictions which are necessary for oral delivery.

The successful transmucosal administration of biphosphonates depends on their specific properties, such as pH, absorption through mucosa, effectiveness and lack of irritability and toxicity. In this respect, the pK of the bisphosphonate compounds has been found ideal for vaginal pH levels. Bisphosphonates have also been found to be compatible with the absorption enhancers and mucoadhesive agents which have been demonstrated with other compounds to promote highly successful delivery of the drug to the systemic circulation. These agents have been found equally effective for enhancement of bisphosphonate absorption and with an improved formulation of the invention led to a substantial increase of efficacy.

Transmucosally delivered bisphosphonates have shown a great therapeutic potential with smaller amounts of these drugs necessary to obtain full therapeutic action. Transmucosally delivered bisphosphonates using the improved formulation have been found to have bioavailability more than 60 times higher than orally administered bisphosphonates.

The method of the invention for transmucosal delivery includes formulating the active pharmaceutical agent, in this case, one of the bisphosphonates, in a reservoir form for daily dosing of from about 0.01 mg to about 3200 mg/day of a selected bisphosphonate, typically in combination with a carrier, preferably the lipophilic carrier, a mucoadhesive, a sorption promoter and/or a penetration enhancer. Due to its excellent vaginal absorption, the bisphosphonate formulation is administered weekly, monthly, quarterly or any other appropriate time interval that supports the therapeutic regimen chosen for a defined bisphosphonates.

A. Types of Bisphosphonates

Generally, all bisphosphonates assert a specific effect on bone structure and formation. Each of the known bisphosphonates has been investigated and the following properties have been described.

1. Alendronate

Alendronate is commercially available from Merck & Co., Inc., Rahway, N.J. as alendronate sodium under the product name FOSAMAX®.

a. Therapeutic Benefits of Alendronate

Alendronate increases bone mineral density (BMD), prevents radiographically defined (morphometric) vertebral fractures and positively affects morphometric as well as clinically evident fractures in postmenopausal women with low bone mass.

b. Disadvantages of Oral Administration

When administered orally, alendronate has been shown to be poorly absorbed though the gastrointestinal tract and to have a bioavailability of less than 1%. When administered in doses ranging between 5–40 mg to women fasting overnight and administered orally 2 hours before first meal of the day, its bioavailability has been found to be as low as 0.7%. In men, this value has been reported to be even lower at 0.59%.

The absorption and bioavailability is reduced even further by additional 40% if the compounds are administered 30–60 minutes before the first meal of the day. If administered concurrently with the meal or two hours afterward, the absorption and the drug bioavailability is negligible. Even coffee and orange juice intake results in additional reduced absorption by about 60%.

Additionally to poor absorption and bioavailability, alendronate causes severe irritation of the mucosa of the upper gastrointestinal tract, especially the esophagus, with development of frequent bleeding and ulceration. These symptoms may be reduced by taking at least two cups of water with each tablet at least 60 minutes before the meal. This regimen, understandably proves to be difficult and inconvenient for patients. The patients are also warned not to chew the tablets because of oral or pharyngeal ulcerations. The concurrent use of aspirin and other NSAID's seems to increase the GI symptoms and ulceration.

Up to 10% of the patients in a one-year, highly controlled clinical trial have been reported to have stopped using FOSAMAX® because of side effects and dosing restrictions. Treatment discontinued rates have proven to be much larger (>50%) in actual clinical use of the drug on a non-protocol basis.

As is evident from the above, although alendronate would be very desirable pharmaceutical agent for treatment of osteoporosis and Paget's disease, its use is necessarily limited due to its poor absorption and bioavailability and not the least by the development of severe health complications.

c. Transmucosal Delivery of Alendronate Therapeutic Formulation

The current invention provides alendronate in a improved transmucosal vaginal formulation suitable for transmucosal administration either directly in a form of a vaginal suppository, foam, cream, tablet, capsule, ointment, gel or microcapsules or indirectly to be administered via a vaginal device. Alendronate daily dose for oral administration is from about 5 to about 40 mg/day administered once, twice or as many times/day, week, month or quarterly, as needed. The formulation is, preferably, in a sustained release form to provide a continuous and sustained release of the drug from the formulation. However, to provide a daily supply of the drug, the drug may be formulated for a rapid release and transmucosal absorption.

An improved formulation of the invention contains from 0.05 to 40 mg of alendronate/day.

2. Clodronate

Clodronate is commercially available from Roche Diagnostics GmbH (Mannheim, Germany). Currently, clodronate is administered intravenously or orally.

a. Therapeutic Benefits of Clodronate

Clodronate has been shown to inhibit increases in bone resorption and to prevents bone loss due to the menopause and during immobilization. Short-term and long-term studies indicate that clodronate stops bone loss at the lumbar spine in patients with vertebral osteoporosis. Treatment with clodronate induces a gain in bone mass, especially in the spine. Even high doses of clodronate do not impair the mineralization of bone, making it suitable for long-term use in osteoporosis.

Clodronate treatment has also been shown to decrease bone turnover and to attenuate cancer-related bone morbidity. In addition, clodronate increased BMD in apparently unaffected bone of women with relapsing breast cancer.

b. Disadvantages of Oral Administration

As is evident from the above, clodronate is a potent pharmaceutical agent for treatment of osteoporosis and Paget's disease. However, as with other bisphosphonates, it shows poor absorption and bioavailability as well as irritability of esophagus and, therefore, its use is necessarily limited due to development of adverse reactions.

c. Transmucosal Delivery of Clodronate Therapeutic Formulation

The current invention provides clodronate in an improved transmucosal vaginal formulation suitable for transmucosal administration either directly in a form of a vaginal formulation such as vaginal suppositories, creams, foams, tablets, capsules, ointments, gels or microcapsules or indirectly as a formulation incorporated into a vaginal device of the invention to be administered via said transmucosal device. Clodronate daily dose for oral administration is from about 100 to about 3200 mg/day administered once, twice or as many times/day, week, month or quarterly, as needed. The formulation is, preferably, in sustained release form to provide a continuous and sustained release of the drug from the formulation. However, to provide a daily supply of the drug, the drug may be formulated for a rapid release and transmucosal absorption.

The improved formulation contains about 1 to 3200 mg/daily dose of clodronate.

3. Etidronate

Etidronate is commercially available from Procter & Gamble Pharmaceuticals (Cincinnati, Ohio).

a. Therapeutic Benefits of Etidronate

Etidronate is suitable for treatment of patients with corticosteroid induced osteoporosis as it prevents loss of vertebral bone density in these patients. Therapy with cyclical etidronate plus ergocalciferol prevented glucocorticoid-induced bone loss and even increased lumbar spine and femoral neck BMD in postmenopausal women commencing glucocorticoid therapy.

After one year of open-label treatment, patients previously treated with etidronate maintained bone mass, and occurrence of vertebral fracture rates in all groups were lower than in any other study period. Three years of intermittent cyclic etidronate therapy produced significant increases in spinal and hip bone density, with a significant reduction in vertebral fracture rates in patients at higher fracture risk. Maintenance of bone mass and low fracture rate were observed when etidronate was continued for another year.

b. Disadvantages of Oral Administration

Although there were no serious adverse effects observed from etidronate use, and etidronate was found to be a potent pharmaceutical agent for prevention and treatment of osteoporosis and loss of vertebral bone density, as with other bisphosphonates, etidronate shows low absorption from GI tract and bioavailability. Therefore, its use is necessarily limited and increase in its bioavailability would improve its therapeutic utility.

c. Transmucosal Delivery of Etidronate Therapeutic Formulation

The current invention provides etidronate in an improved transmucosal vaginal formulation suitable for transmucosal administration either directly as an transmucosal formulation in a form of vaginal suppositories, creams, tablets, ointments, gels or microcapsules or indirectly to be administered via a vaginal device of choice, as described below. Etidronate daily dose for oral administration is from about 5 to about 20 mg/day administered once, twice or as many times a day, week, month or quarterly, as needed. The formulation is, preferably, formulated in a sustained release form to provide a continuous and sustained release of the drug from the formulation. However, to provide a daily supply of the drug, the drug may be formulated for a rapid release and transmucosal absorption.

The improved formulation contains from about 0.05 to about 20 mg/kg daily dose of etidronate.

4. Pamidronate

Pamidronate (aminohydroxypropylidine bisphosphonate, APD) is commercially available from Novartis, Basel, Switzerland.

a. Therapeutic Benefits of Pamidronate

Pamidronate is an effective agent for treatment of Paget's disease of bone, and it is also effective for treatment of osteoporosis. Long-term treatment with an orally administered pamidronate overcomes bone loss and increases bone mass when compared with placebo and may be suitable for the treatment of patients with rheumatoid arthritis. Long-term uninterrupted treatment of patients with osteoporosis with oral pamidronate is associated with increases in bone mineral content (BMC) of the lumbar spine and with an additional effect of the treatment on skeletal tissue.

Administration of suppressive doses of the pamidronate to patients with excessive osteoclastic resorption is followed by transient decreases in serum calcium and increases in parathyroid hormone (PTH) concentrations. Chronic pamidronate therapy thus may stimulate PTH secretion, which in turn has been previously shown to have anabolic effects on the skeleton.

b. Disadvantages of Oral Administration

Pamidronate is known to cause esophagitis in treated patients and, although it is a potent pharmaceutical agent for prevention and treatment of Paget's disease, osteoporosis and for increasing bone mass, as with other bisphosphonates, it shows poor absorption and bioavailability as well as irritability and ulceration of esophagus. Therefore, the clinical use of pamidronate is limited to intravenous administration.

c. Transmucosal Delivery of Pamidronate Therapeutic Formulation

The current invention provides pamidronate in an improved transmucosal vaginal formulation suitable for transmucosal administration. The formulation is provided either directly in a form of a vaginal suppository, cream, tablet, capsule, ointment, gel or microcapsules or indirectly to be administered via a vaginal device. Pamidronate daily dose by intravenous injection/infusion is from about 1 to about 30 mg/day administered once, twice or as many times/day, week, month or quarterly, as needed. The formulation is, preferably, in sustained release form to provide a continuous and sustained release of pamidronate from the formulation. However, to provide a daily supply of pamidronate, it may be formulated for a rapid release and transmucosal absorption.

The improved formulation contains from about 1 to about 3000 mg/daily dose of pamidronate.

5. Tiludronate

Tiludronate (tiludronic acid disodium salt) is commercially available from Sanofi, France.

a. Therapeutic Benefits of Tiludronate

Tiludronate was shown to be effective in reducing bone resorption in several metabolic bone diseases without inducing mineralization defects. The clinical development of tiludronate for the treatment of Paget's disease of bone have shown that tiludronate is equally suitable for treatment of osteoporosis. Osteoporosis becomes a major indication for tiludronate.

b. Disadvantages of Oral Administration

As is evident from the above, although tiludronate is a very good pharmaceutical agent for treatment of osteoporosis and Paget's disease, its use is necessarily limited due to its poor absorption and bioavailability and not the least by the development of adverse reactions.

c. Transmucosal Delivery of Tiludronate Therapeutic Formulation

The current invention provides tiludronate in an improved transmucosal vaginal formulation suitable for transmucosal administration either directly in a form of a vaginal suppository, cream, tablet, ointment, gel or microcapsules or indirectly by incorporation, said, formulation into the transmucosal device of the invention. Tiludronate daily dose for oral administration is from about 2 to about 400 mg, administered once, twice or as many times/day, week, month or quarterly, as needed. The formulation is, preferably, in sustained release form to provide a continuous and sustained release of the drug from the formulation. However, to provide a daily supply of the drug, the drug may be formulated for a rapid release and transmucosal absorption.

The improved formulation of the invention contains from about 0.02 mg to about 400 mg/kg daily dose of tiludronate.

6. Ibandronate

Ibandronate is commercially available from Roche Diagnostics GmbH (Mannheim, Germany).

a. Therapeutic Benefits of Ibandronate

A new, third generation bisphosphonate ibandronate is preferentially useful for treatment of postmenopausal osteoporosis. Ibandronate treatment increases bone mass in all skeletal regions in a dose dependent manner with 2.5 mg/daily being the most effective dose. Ibandronate treatment reduces bone turnover to premenopausal levels and is well tolerated.

b. Disadvantages of Oral Administration

As is evident from the above, although ibandronate is a potent pharmaceutical agent for treatment of osteoporosis and Paget's disease, its use is necessarily limited due to its poor absorption and bioavailability.

c. Transmucosal Delivery of Ibandronate Therapeutic Formulation

The current invention provides ibandronate in an improved transmucosal vaginal formulation suitable for transmucosal administration either directly in a form of a vaginal suppository, cream, tablet, ointment, gel or microcapsules or indirectly to be administered via a vaginal device. Ibandronate daily dose by intravenous injection/infusion or oral administration is from about 0.05 mg to about 50 mg/day administered once, twice or as many times as needed. The formulation is, preferably, in sustained release form to provide a continuous and sustained release of the drug from the formulation. However, to provide a daily supply of the drug, the drug may be formulated for a rapid release and transmucosal absorption.

The improved formulation contains from about 0.01 to about 50 mg daily dose of ibandronate.

7. Neridronate

Neridronate is commercially available.

a. Therapeutic Benefits of Neridronate

Neridronate is a third generation amino-bisphosphonate useful for treatment and prevention of osteoporosis as well as collagen disease.

b. Disadvantages of Oral Administration

Although neridronate is an effective pharmaceutical agent for treatment of osteoporosis and collagen related diseases, its use is exclusively limited to intravenous administration due to its poor absorption and bioavailability.

c. Transmucosal Delivery of Neridronate Therapeutic Formulation

The current invention provides neridronate in an improved transmucosal vaginal formulation suitable for transmucosal administration either directly in a form of a vaginal suppository, cream, tablet, ointment, gel or microcapsules or indirectly to be administered via a vaginal device. Neridronate preferred daily dose by intravenous injection/infusion is from about 0.01 to about 0.7 mg/day administered once, twice or as many times/day as needed. The formulation is, preferably, in sustained release form to provide a continuous and sustained release of the drug from the formulation. However, to provide a daily supply of the drug, the drug may be formulated for a rapid release and transmucosal absorption.

The improved formulation contains from about 0.1 to about 150 mg daily dose of neridronate.

8. Risedronate

Risedronate is commercially available from Procter & Gamble Pharmaceuticals (Cincinnati, Ohio).

a. Therapeutic Benefits of Risedronate

Risedronate is a third generation bisphosphonate useful for treatment and prevention of osteoporosis.

b. Disadvantages of Oral Administration

Although risedronate is an effective pharmaceutical agent for treatment of osteoporosis and related diseases, its use is limited due to its rapid absorption resulting in unpredictable bioavailability.

c. Transmucosal Delivery of Risedronate Therapeutic Formulation

The current invention provides risedronate in an improved transmucosal vaginal formulation suitable for transmucosal administration either directly in a form of a vaginal suppository, cream, tablet, ointment, film, foam, gel or microcapsules or indirectly to be administered via a vaginal device. Risedronate preferred daily dose for oral administration is from about 5 to about 30 mg/day administered once, twice or as many times/day as needed. The formulation is, preferably, in sustained release form to provide a continuous and sustained release of the drug from the formulation. However, to provide a daily supply of the drug, the drug may be formulated for a rapid or slow release and transmucosal absorption.

The improved formulation contains from about 0.05 to about 30 mg daily dose of risedronate.

8. Other Currently Available Bisphosphonates

Currently zoledronic acid (Novartis Pharma AG, Basel, Switzerland; 4 mg daily intravenous dose), olpadronate (Gador Pharmaceutical Laboratories, Buenos Aires, Argentina; 200 to 400 mg daily oral does), incadronate (Yamanouchi Pharmaceuticals, Tokyo, Japan; 10 mg daily intravenous does), and minodronate (Yamanouchi Pharmaceuticals, Tokyo, Japan; no clinical data available) are under development for similar therapeutic use as described for other bisphosphonates.

These bisphosphonates are formulated as improved transmucosal vaginal formulations according to the invention.

C. Pharmacokinetics of Vaginal Delivery of Bisphosphonates

Vaginal delivery of alendronate was investigated in the rabbit model. Since the systemic bioavailability of alendronate, a potent antiosteolytic bisphosphonate, is generally below 1% when the dose is administered via the oral route, one of the objectives of this study was to determine whether the delivery of alendronate across the vaginal mucosa has the potential to significantly improve the systemic bioavailability of this drug. Another objective was to determine if a modified transmucosal formulation could increase delivery of bisphosphonate by transmucosal vaginal delivery route.

Figure 2:
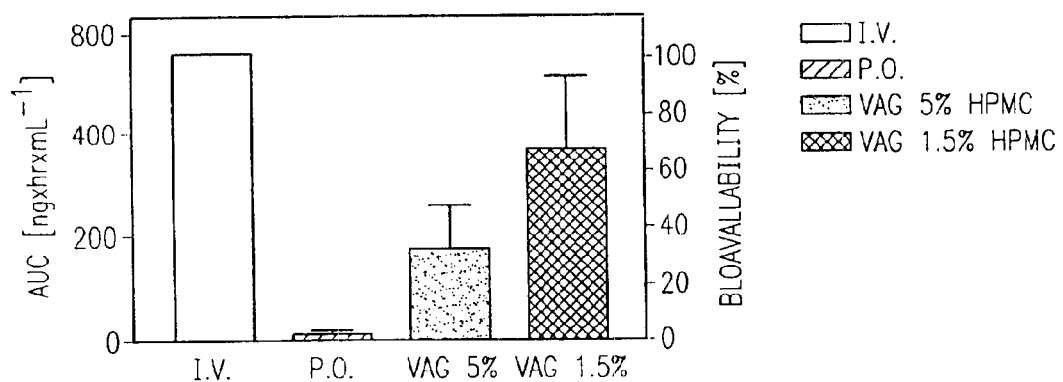
FIG. 2 illustrates an improvement in bioavailability, in percent, of alendronate in plasma of a female white New Zealand rabbit following an oral, intravenous or vaginal transmucosal administration of alendronate using a prior (5% HPMC) and an improved (1.5% HPMC) formulation.

Plasma pharmacokinetic of alendronate was determined in anesthetized female white New Zealand rabbits after intravenous, vaginal, and peroral administration (dose= 0.14–0.21 mg/kg) according to Example 1. Four parameters were studied and compared, namely peroral, intravenous and vaginal administration using a prior (5% HPMC) and improved (1.5% HPMC) formulation. For analytical purposes, each dose was supplemented with a trace amount of [$^{14}$C]alendronate. Model-dependent pharmacokinetic parameters were calculated using WinNonlin from plasma concentrations of alendronate collected for 24 hours. Results are illustrated in FIGS. 1 and 2 and in Table 1.

TABLE 1

Pharmacokinetic Parameters of Alendronate in New Zealand Rabbits Following Intravenous, Vaginal, and Peroral Administration

| Parameter | Intra-venous | Vaginal 1.5% HPMC | Vaginal 5% HPMC | Peroral |
|---|---|---|---|---|
| Dose [mg × kg$^{-1}$] | 0.15 | 0.15 | 0.15 | 0.21 |
| C$_{max}$ [ng × mL$^{-1}$] | 1189.8 | 104.5 ± 43.8 | 34.8 ± 16.0 | 1.6 ± 1.0 |
| t$_{max}$ [hr] | 0 | 0.5 ± 0.1 | 0.6 ± 0.1 | 4.7 ± 2.1 |
| AUC [ng × hr × mL$^{-1}$] | 559.2 | 372.9 ± 145.4 | 180.0 ± 82.4 | 14.1 ± 6.4 |
| t$_{1/2}$ [hr] | 0.3 | 4.0 ± 2.3 | 7.8 ± 0.9 | 9.3 ± 3.2 |
| F | 100 | 67.1 ± 26.2 | 30.1 ± 13.4 | 1.8 ± 0.8 |

Pharmacokinetic parameters were calculated from plasma drug concentrations using the model-dependent analysis module of WinNonlin.

Table 1 lists pharmacokinetic parameters observed in plasma of white New Zealand rabbits following the intravenous, transmucosal vaginal and oral administration of alendronate in doses 0.15 mg/kg for intravenous, 0.15 mg/kg for vaginal and 0.21 mg/kg for oral route of administration. Two formulations were investigated for transmucosal vaginal delivery, namely the prior (5% HPMC) and improved (1.5% HPMC) formulation. Table 1 further shows maximal plasma concentration (C$_{max}$), area under the curve (AUC) in ng×hr×mL$^{-1}$, an apparent half-life (t$_{1/2}$/hr) and bioavailability (F).

As seen in FIG. 1, after intravenous administration of alendronate in a saline solution, alendronate rapidly disappeared from the vascular system with an apparent half-life of 0.3 hours. This is consistent with earlier observations in various other species and relates to the high affinity of this drug to the bone.

When delivered vaginally using a suppository that was formulated either with 5% HPMC (prior) or with 1.5% HPMC (improved), plasma concentrations of alendronate rapidly increased to reach a maximum around 0.5 hr, as seen in FIG. 1. Area under the curve for the prior (5% HPMC) formulation was 180 mg×hour×mL$^{-1}$. Area under the curve for the improved formulation was 372.9 mg×hour×mL$^{-1}$. From the area under the plasma concentration time curve (AUC), the mean absolute bioavailability that was calculated for the prior formulation using transmucosal vaginal of administration was 30.1% (5% HPMC) and 67.1% the improved formulations.

The mean absolute bioavailability (F%) of alendronate in rabbits following the oral administration was 1.8%. Following the vaginal administration of the prior transmucosal (5% HPMC) formulation was 30.1% and 67.1% for improved transmucosal formulation. Bioavailability following intravenous administration is per definition 100%.

Clearly, vaginal transmucosal delivery of alendronate is significantly more effective than oral delivery and transmucosal delivery using the improved (1.5% HPMC) formulation is twice as effective as the transmucosal delivery using prior transmucosal formulation (5% HPMC). To achieve plasma concentrations of alendronate through a transmucosal vaginal administration that are equivalent to the drug concentrations measured following oral administration, approximately 3.5% of the oral dose would be sufficient for vaginal administration. As a substantial benefit for the patient, because of the 67 times increased absorption into the systemic circulation by the vaginal delivery, the transmucosally delivered bisphosphonates may be delivered weekly, monthly, quarterly or using any other appropriate time interval that supports the therapeutic regimen chosen for a defined bisphosphonate. The vaginal administration of alendronate can significantly reduce the severe side effects that are characteristic for the drug class of bisphosphonate.

FIG. 1 shows concentration-time profiles of alendronate in plasma following vaginal administration of either the prior (-•-) or improved (-o-) formulation comprising a single dose of alendronate of 0.15 mg/kg$^{-1}$ to female white New Zealand rabbits. These studies were performed at least in triplicate and the values given are average ± SEM.

As seen from FIG. 1, the administration of the prior (-•-) formulation raised concentrations to about 0.03 μg/ml of alendronate in plasma during the first hour. Such increase was relatively low and decreased to almost zero level after the first six hours, resulting in approximately 30% bioavailability of alendronate. The transmucosal vaginal administration of the improved formulation (-o-) resulted in rapid increase of alendronate in plasma, reaching its peak (~0.1 μg/ml) in less than one hour after administration and decreasing slowly during 24 hours, reaching bioavailability values of about 67.7%. More than two times more alendronate was present and available in plasma following the vaginal delivery of a suppository formulated with 1.5% HPMC, when compared to the levels of alendronate available in plasma following vaginal delivery of the same amount of alendronate in the prior (5% HPMC) transmucosal formulation.

These results are unexpected and surprising and confirm that the efficacy of the transmucosal vaginal delivery is dependent on the formulation. Combined with elimination of adverse reactions observed during oral delivery, the vaginal transmucosal delivery using the improved formulation is much better way to administer bisphosphonates.

FIG. 2 is a graphical illustration of bioavailability (67.7%) of alendronate observed following administration of alendronate as the oral formulation (1.8%), as vaginal prior formulation (30%), as vaginal improved (67.1%) formulation and as intravenous formulation (100%).

As seen from the above results, the vaginal transmucosal delivery is clearly superior to the oral delivery and eliminates all adverse effects accompanying the oral administration. Because of the unique formulation consisting of the lower amounts of mucoadhesive agent, in the presence of a penetration enhancer and an inert lipophilic carrier, the poor absorption across the GI mucosa is overcome, and the bisphosphonate is delivered to a significantly greater extent through the vaginal mucosa directly to the systemic circulation. This delivery route is also preferable to the intravenous route because it is noninvasive.

According to the invention, bisphosphonates which are brought into contact with the vaginal mucosa formulated in an improved formulation are made more bioavailable. The method for transmucosal delivery of bisphosphonates is eminently suitable for the treatment of osteoporosis, Paget's disease, other diseases of bone and skeleton, bone fractures and bone metastatic and nonmetastatic bone disease.

II. Compositions, Formulation and Devices for Vaginal Delivery

The primary purpose of this invention is to enhance the systemic delivery of a series of bisphosphonates which have poor bioavailability and a high level of gastrointestinal toxicity, both for treating and preventing the osteoporosis and related diseases of bone and skeleton.

A. Formulations for Transmucosal Vaginal Delivery of Bisphosphonates

Formulations for transmucosal vaginal administration and delivery typically comprise a bisphosphonate drug present in about 0.01 to about 3200 mg, depending on the particular bisphosphonate, a lipophilic or hydrophilic, preferably the lipophilic, carrier present in about 40–95%, preferably about 60–85% (w/w), most preferably above 68.5% mucoadhesive agent present in about 0.01 to up to about 5%, preferably from about 1–3%, most preferably from about 1.5% (w/w), penetration enhancer or sorption promoter present in 5–25%, preferably from about 10–20% and most preferably about 15% (w/w) concentration and, optionally, a solubilizer from about 5–25%, preferably from about 3–15%.

Other excipients, such as water, water for injection, saline, additives, fillers, coloring agents, or other pharmaceutically acceptable and/or therapeutically effective compounds may also be added to the formulations of the invention.

1. Pharmaceutical Agents

A pharmaceutical agent suitable for transmucosal delivery is any bisphosphonate known now as described above or discovered later which may be formulated with a drug delivery system according to the invention.

Pharmaceutical agents for use in the invention are absorbable through the vaginal mucosa into the circulation system. The pharmaceutical agent is preferably selected from the group consisting of bisphosphbnates alendronate, risedronate, clodronate, pamidronate, etidronate, tiludronate, neridronate, ibandronate, olpadronate, zoledronic acid, incadronate and minodronate.

2. Excipients and Carriers

A formulation for transmucosal administration typically comprises a suitable biocompatible excipient for formulating a selected bisphosphonate, which excipient includes a lipophilic carrier, a hydrophilic carrier, a mucoadhesive agent, a penetration enhancer and, optionally, a solubilizer.

In order to achieve desirable drug release, the active ingredient i.e. a bisphosphonate is incorporated into an excipient (i.e., vehicle or carrier) for which the drug has low affinity. Hence, hydrophilic drugs are incorporated into lipophilic carriers, and lipophilic drugs will be incorporated into hydrophilic carriers. Bisphosphonates are primarily hydrophilic drugs, therefore, they are typically incorporated into lipophilic carriers.

Preferred lipophilic carriers for use with hydrophilic drugs include semi-synthetic glycerides of saturated fatty acids, particularly fatty acids of eight to eighteen carbons, such as SUPPOCIRE® AS2, as defined above, commercially available, for example, from Gattefossé, Westwood, N.J., and other suitable hard fats and carriers. The lipophilic carrier is present in the improved formulation in about 40–95%, preferably 60–80%, and most preferably about 68.5%(w/w).

The system of the invention preferably also comprises a mucoadhesive agent to bring the released drug in solution into prolonged, close contact with the mucosal surface. The muco-adhesive agent is preferably hydroxypropyl methylcellulose (HPMC). HPMC may be in combination with a polymer such as an alginate, pectin, or another cellulose derivative. The mucoadhesive agent for the formulation of the current invention is preferably HPMC present in amount lower than 5%, preferably between 0.5–3%, and most preferably about 1.5%.

The system of the invention may also additionally include a penetration enhancer or sorption promoter to enhance permeation of the drug across the vaginal mucosa. Preferred sorption promoters include nonionic surface active agents, bile salts, organic solvents, interesterified stone oil, and particularly ethoxydiglycol, commercially available, for example, as TRANSCUTOL® from Gattefossé, or interesterified stone oil, commercially available, for example, as LA BRAFIL® M 1944CS from Gattefosse. Most preferred is ethoxyglycol present in about 5 to 25%, preferably about 15% (w/w).

Additionally and optionally, the formulation may comprise a solubilizer, such as Tween, a polyoxethylene castor oil derivative, cyclodextrine, polyoxethylene alkyl ester, glyceryl monostearate, lecithin, poloxamer, polyoxethylene stearate and a sorbitan ester present in about 1–10%.

B. Drug Delivery Systems

The vaginal drug delivery systems of the invention provide an effective and time-controlled delivery of the drug across the vaginal mucosa into the systemic circulation.

1. Types of Delivery Systems

The delivery system can be a solid object delivery system such as a tampon, tampon-like device, vaginal ring, strip, cup, pessary, vaginal applicator, tablet or suppository. Alternatively, it can be a semi-solid or liquid formulation in the form of paste, cream, ointment, film, foam, suspension, solution, capsule, microparticle, nanoparticle, bioadhesive, gel or capsule containing micro/nanoparticle having a sufficient thickness to maintain prolonged contact with vaginal mucosa. Alternatively, for example, it can be a coating on a suppository wall, coating on tampon applicator or a sponge or other absorbent material impregnated with a liquid drug containing solution, lotion, or suspension of bioadhesive particles. Any form of drug delivery system which will effectively deliver the treatment agent to the vaginal endothelium is intended to be included within the scope of this invention.

For purposes of simplifying the description of the invention and not by way of limitation, tampon and suppository drug delivery systems will be described hereinafter, it being understood that all effective delivery systems are intended to be included within the scope of this invention.

2. Controlled Release Drug Delivery

The controlled release drug delivery system according to the invention is capable of controlling the rate of release of drug in solution for absorption across the vaginal mucosa into the systemic circulation. The release rate has been optimized to match drug distribution, inactivation, and elimination, so that nearly constant plasma and tissue levels are maintained while the drug is in the vagina. Appropriate excipients known to a person skilled in the art can be incorporated to achieve the desired controlled release. For example, if the pH in the vaginal cavity changes, this fact must be taken into consideration when the delivery system is designed. Drug delivery systems with buffers to enhance absorption are included in the present invention. Additionally, the system, for example the tampon, should be easily removable, for example, attached to a string, applicator or tape.

3. Bioadhesive Systems

Bioadhesive particulate delivery systems constitute still another transmucosal drug delivery system suitable for use in the present invention.

The bioadhesive systems consist of natural polymers, such as cellulose derivatives, synthetic polymers, such as polyacrylic acid, or combinations thereof, and control the release of bisphosphonates over several days following placement into the vaginal cavity. This system represents a multi-phase liquid, semi-solid, or solid preparation or a combination thereof, which does not leak from the vagina as do most current suppository formulations. The bioadhesive particulate delivery systems cling to the wall of the vagina and release the drug over a controlled time period ranging from several hours to several days. Many of these systems were designed for nasal use, as described in U.S. Pat. No. 4,756,907, incorporated herein by reference, but can be easily modified for use in the vagina. The bioadhesive particulate delivery system may comprise, for example, microparticles filled with the bisphosphonate and may contain a sorption promoter for enhancing transmucosal transport of the drug into the systemic circulation. The microparticles have a diameter of 1 to several 100 $\mu$m and can be prepared from starch, gelatin, albumin, dextran, cellulose derivatives, or synthetic polymers such as polyacrylic acid according to methods known in the art.

C. Formulations

Formulations of the invention are specific for transmucosal delivery of the formulation of the invention. The formulation is, therefore, directed to specific requirements of the transmucosal release of the drug from the formulation, for bringing the drug into a close proximity or in contact with the vaginal mucosa and for promoting penetration, absorption, transfer or transport of the drug through the vaginal mucosa.

Typically, therefore, the formulation will be formulated with a lipophilic or hydrophilic carrier suitable for selected bisphosphonate, a low amount of a mucoadhesive agent which increases contact with vaginal epithelium and enables adhesion of the drug or drug carrier complex to the vaginal mucosa, and, additionally, since the penetration, absorption, transfer or transport of the bisphosphonate to the systemic circulation is mandatory in this invention, the formulation also contains a penetration enhancer or sorption promoter to enable such penetration, absorption, transfer or transport through the mucosa.

3. Representative Formulation

The formulations listed below have been prepared and tested, but are listed here only for purposes of illustrating the formulations of the invention. They are not intended to be in any way limiting and all formulations falling within the scope of the ranges listed above are intended to be within the scope of the invention.

The transmucosal formulation of the invention comprises, in one embodiment of the invention, a bisphosphonate between about 0.01 and 10%, by weight, and about 90–99% of the excipient comprising between about 60 to 90%, by weight, lipophilic or hydrophilic (if appropriate) carrier, between about 0.01 to about 5%, by weight, mucoadhesive agent, and between about 5 to 25%, by weight, penetration enhancer.

In another embodiment of the invention, the formulation comprises a bisphosphonate about 0.01–10%, by weight, and about 90–99% the excipient comprising between about 60 to 80%, by weight, carrier, between about 0.1 to 3%, by weight, mucoadhesive agent, and between about 10 to 20%, by weight, penetration enhancer.

In most preferred embodiment of the invention, the formulation comprises about 0.01–5% bisphosphonate formulated into a vaginal suppository which includes about 68.5% of a lipophilic carrier SUPPOCIRE® AS2, about 1.5% of mucoadhesive hydroxypropyl methylcellulose, and about 15% of penetration enhancer TRANSCUTOL®.

Additionally, the formulation may comprise other biocompatible excipients, such as glycerin, mineral oil, polycarbophil, carbomer 934P, hydrogenated palm oil, glyceride, sodium hydroxide, sorbic acid, and purified water.

2. Other Formulation

The bisphosphonate can be incorporated into creams, lotions, foams, paste, ointments, solutions, suspensions and gels which can be applied to the vagina using an applicator. Processes for preparing pharmaceuticals in cream, lotion, foam, film, paste, ointment and gel formats can be found throughout the literature.

Suitable nontoxic pharmaceutically acceptable systems for use in the formulations of the present invention will be apparent to those skilled in the art. This includes all pharmaceutical formulations and examples described in Remington's *The Science and Practice of Pharmacy*, 20th Edition, A. R. Gennaro, Ed., (2000), *The Theory and Practice of Industrial Pharmacy*, Lachman, Lieberman and Kanig and *Pharmaceutical Dosage Forms*, Liberman and Lachman.

The choice of suitable carriers will depend on the exact nature of the particular vaginal dosage form desired, e.g., whether the active ingredients(s) is/are to be formulated into a cream, lotion, foam, ointment, paste, solution, suspension or gel, as well as on the identity of the active ingredient(s).

3. Process for Preparation of Bisphosphonates Formulations

The alendronate sodium is dissolved in the water and set aside. The SUPPOCIRE® is melted in 50° C. water bath. The TRANSCUTOL® is added with stirring, followed by the HPMC. The alendronate sodium solution is added last with stirring. The heated mixture is poured in suppository molds and cooled.

D. Devices for Transmucosal Drug Delivery

The device of the invention can be in the form of, for example, a tampon-like device, vaginal ring, vaginal pessary, vaginal tablet, paste, vaginal suppository, vaginal sponge, bioadhesive tablet, bioadhesive microparticles, incorporated with a formulation comprising a bisphosphonate. Each of these systems is discussed below.

1. A Tampon or Tampon-Like Device

In one embodiment, the invention provides a tampon device for delivering a pharmaceutical agent to the vagina comprising an absorbent vaginal tampon having a proximal end and a distal end. A cup-shaped porous foam portion at the distal end fits around the cervix of the uterus and contains a pharmaceutical agent for delivery to the fornix areas. However, said formulation may also be incorporated into the proximal end of the tampon. The device may also include a nonabsorbing axial tube having a distal opening and extending through the porous foam cup into the tampon. A retrieval string or tape connected to the tampon device may also be included. The absorbent vaginal tampon may contain any of the above-mentioned bisphosphonates and be used as a medicated tampon for individual drug or drug combination delivery.

In another embodiment of a tampon device, the distal porous foam cup has a rim which encircles the cervix. The rim has high concentrations of medication and is designed to release the bisphosphonate unidirectionally towards the mucosal surface of the vagina.

In another embodiment of a tampon device, the distal porous foam cup has a rim which encircles the cervix. The rim has fingers extending into the fornix areas around the cervix and the tips of the fingers have high concentrations of medication for unidirectional delivery of the bisphosphonate to the vaginal mucosa.

In another embodiment of a tampon device, a distal porous foam section is in the shape of a scoop, which only partially encircles the cervix. The porous foam scoop has a nib-like shape which is designed to wedge itself into the posterior fornix. The porous foam scoop is designed to deliver medication to the vaginal wall along the entire length of the porous foam scoop.

In another embodiment, a tampon device is sheathed in a thin, supple, non-porous material such as a plastic film or a coated gauze or, in alternative, an applicator that surrounds the absorbent tampon material like a skirt and opens like an umbrella when it comes in contact with the vaginal environment. A band of drug, ideally suspended in a wax-like carrier that melts at body temperature, encircles the sheathed tampon or is applied, for example, on the applicator inner or outer wall. Contact with vaginal fluids or causes the tampon to swell, forcing the skirt to open like an umbrella and to press tightly against the vaginal wall, putting the drug in contact with the vaginal mucosa while effectively preventing the drug from being absorbed into the tampon.

In another embodiment of a tampon device, distal fibers of the tampon which contact the vaginal surface have high concentrations of pharmaceutical agent for delivery of the agent into the systemic circulation.

In another embodiment of a tampon device, the tampon device has an outer tubing having perforations, the outer tubing is concentric around an axial tube. The device has a distal porous foam section which in its dehydrated state is tight around the outer tubing. A bladder is located proximally to the porous foam and filled with liquid pharmaceutical agent. The bladder is connected to the outer tubing. An outer sheath covers the tampon. The sheath has an annular constriction distal to the bladder such that deployment of the tampon through the distal end of the sheath causes the liquid in the bladder to be forced out distally through the perforated outer tubing and into the porous foam.

In another embodiment of a tampon device, the tampon device has an annular delivery formulation around the distal end. The formulation contacts the vaginal epithelium for delivery of the agent. A non-absorbing axial tube opens distally and extends into the tampon for conducting vaginal secretions to the absorbent material proximal to the porous foam. The annular formulation can be a suppository, foam, paste, or gel.

Embodiments of the invention may include tampon devices of a standard length, or may be longer than standard tampons to facilitate locating the tampon device closer to or in contact with the fornix areas.

It is to be understood that all devices described herein are incorporated with an improved transmucosal vaginal formulation comprising a selected bisphosphonate.

Devices of the invention are illustrated in FIGS. 3–21.

FIG. 3 is a cross-sectional representation of a portion of the female reproductive organs, including the uterus and the vagina in the upright orientation, and FIG. 4 is a cross-sectional side view representation thereof. The uterus 2 is a muscular organ enclosing the womb 4, and opening at the cervix 5 via the cervical canal or cervical os 6. The vagina 8 is defined by a muscular tube 10 leading from the labia minora 12 and labia majora 14 to the cervix 5. The local vasculature associated with the walls of the vagina 8 communicate with the uterine muscle vascular and lymphatic systems (not illustrated).

FIG. 5 is a cross-sectional representation of FIG. 3 showing placement of a drug delivery system 16 in the vagina 8, a position which introduces drugs transmucosally to the systemic circulation by way of the vaginal blood vascular and lymphatic systems. Physiologically, this concept has been documented and confirmed in animal experiments reported herein.

Referring now to FIGS. 6–14, there being depicted various embodiments of tampon-like devices which can be used to deliver drugs for prevention and treatment of osteoporosis, Paget's disease, and other diseases of bone and skeleton or cancer according to the invention. If a tampon-like device is used, there are numerous methods by which a drug can be incorporated into the device. For example, the drug can be incorporated into a gel-like bioadhesive reservoir on the device or attached as a strip to the tampon. Alternatively, the drug can be positioned at various locations of the tampon. The drug can also be absorbed to fibers of the tampon, for example, by dissolving the drug in a pharmaceutically acceptable carrier and absorbing the drug solution into the tampon fibers. The drug can also be dissolved in a coating material which is applied to the tampon. Alternatively, the drug can be incorporated into an insertable suppository which is placed in association with the tampon.

The tampon-like device can be constructed so as to improve drug delivery. For example, the tampon can be shaped to fit in the area of the posterior fornix and pubic symphysis and constructed so as to open up to have maximum surface area of contact for drug delivery. If the drug is in a reservoir on the surface of the device, the shape of the device should be such that it can maintain the reservoir towards a vaginal mucosal orientation for best predictable drug release characteristics.

The tampon device can also be constructed so as to have a variable absorption profile. For example, the drug area at the tip of the tampon device could be different from that of the more proximal area in order to force the drug to diffuse out into tissue, as opposed to down into the absorbent part of the tampon. Alternatively, there could be a non-absorbing channel around the cervix for the first centimeter or so in order to minimize from washing away the drug formulation.

The release of drug from the tampon device should be timed to provide proper systemic concentrations of the drug over a typical length of use of a tampon device, usually 1–8 hours.

FIG. 6 is a cross-sectional representation of the vaginal area, adjacent the cervix 5, with a first embodiment of a tampon drug delivery system according to the invention. The tampon device 22 comprises an absorbent cylindrical tampon 24 comprised of fibrous material, for example cotton, having around its distal end 26 an annular delivery formulation 28. The tampon device 22 places the annular delivery formulation 28, supported around the distal end 26 of the tampon device 22, against the upper epithelium 18 of the vagina 8 and posterior fornix 20 for delivery through the vaginal surfaces in which the annular formulation 28 is in contact. The annular formulation 28 can be an annular suppository, foam, paste, or gel composed of suitable delivery components.

FIG. 7 is a cross-sectional representation of the vaginal area adjacent the cervix 5 with a second embodiment of a tampon drug delivery system according to the invention. In this embodiment, tampon device 32 includes a non-porous tube 34 which communicates with the cervical os 6 for delivery of the discharge from the cervical os to an absorbent cylindrical tampon 36 comprised of fibers, for example cotton, for absorbing the discharge. The tube 34 prevents contact of the discharge with an annular drug delivery formulation 38.

FIG. 8 is a cross-sectional representation of the vaginal area adjacent the cervix 5 with a third embodiment of a tampon drug delivery system according to the invention. In FIG. 8, the tampon device 42 includes a distal porous foam section 43 which is in the shape of a cup in the expanded state. In the center of the porous foam section 43 is a non-porous tube 44 which will conduct discharge to absorbent tampon 45 proximal to the porous foam section 43. The porous foam is preferably a soft, light weight, physiologically inert foam material of polyurethane, polyester, polyether, (e.g., as described in U.S. Pat. No. 4,309,997) or other material such as collagen (e.g., as described in U.S. Pat. No. 5,201,326). The axial tube is preferably a non-absorptive physiologically inert material, such as rubber or plastic, and can be coated on its inner surface with an anticoagulant. The proximal end 46 of the tube 44 has a plastic loop 47 to which a string 48 may be tied for removal of the tampon device 42. The cup-shaped porous foam section 43 fits around the cervix 5 of the uterus 2 and contains medication which may be delivered to the systemic circulation.

FIG. 9A is a cross-sectional representation of the vaginal area adjacent the cervix 5 with a fourth embodiment of a tampon drug delivery system according to the invention. In FIG. 9A, the tampon device 52 includes a distal porous foam cup 54 and a proximal absorbent tampon 56. The porous foam cup 54 has a rim 58 which encircles the cervix 5, and which contains high concentrations of medication. The rim 58 area of the porous foam cup 54 is away from the direct flow of discharge. The tampon device 52 includes a string 59 for removal of the tampon device 52. FIG. 9B is a cross-sectional view of the embodiment shown in FIG. 9A, taken in the direction indicated by the arrows labeled 9B in FIG. 9A. As illustrated in FIG. 9B, the rim 58 area forms a ring which contains a high concentration of medication. Alternatively, as illustrated in FIG. 10, the entire porous foam cup 55 may contain medication, not just in the ringed tip area 59 near the cervix 5.

FIG. 11A is a cross-sectional representation of the vaginal area adjacent the cervix 5 with a fifth embodiment of a tampon drug delivery system according to the invention. In FIG. 10A, the tampon device 62 includes a proximal absorbent tampon 64 and a distal section 66 which includes a dissolvable suppository or gel capsule 67 filled with liquid medication. The medication prior to dissolution or release of the liquid has a "doughnut" shape to allow for discharge to pass through the center of the tampon 64. The tampon device 62 includes a string 68 attached to the tampon 64 for removal of the tampon device 62. FIG. 11B is a cross-sectional view of the of the embodiment shown in FIG. 11A, taken in the direction indicated by the arrows labeled 11B in FIG. 11A, and illustrates the doughnut shape of the medication filled suppository or gel capsule 67.

FIG. 12 is a cross-sectional representation of the vaginal area adjacent the cervix 5 with a sixth embodiment of a tampon drug delivery system according to the invention. In FIG. 12A, the tampon device 72 includes a porous foam distal section 74 which is in the shape of a cup with "fingers" 76 which extend into the fornix areas 20 around the cervix 5. The tips of the fingers 76 contain high concentrations of medication, which may be delivered to the fornix areas. The tampon device 72 includes a string 79 for removal of the tampon device 72. FIG. 12B is a side view of the porous foam cup 74 and illustrates the fingers 76 which extend into the fornix areas 20 around the cervix 5 (FIG. 12A).

It will be readily apparent to a person skilled in the art that the characterization of the drug delivery device as having an annular shape is only an approximate description of the shape formed by fluid or semisolid drug delivery devices positioned around a cylinder and in contact with adjacent vaginal wall epithelium, and all shapes which conform to the vaginal epithelium and external cervical surfaces are intended to be included within and indicated by the term "annular". Moreover, use of the term "annular" does not restrict the invention to the use of such devices which encircle the entire cervix (i.e. 360 degrees). Devices which span an angle of less than 360 degrees, but which make sufficient contact with the vaginal epithelium to deliver sufficient quantity of the drug are within the scope of the invention.

The annular drug delivery formulation (FIGS. 6 or 7) can be an absorbent material which expands in the presence of fluid or body heat to completely fill the space between the tampon 22, 32 and the vaginal epithelium 18.

FIG. 13 illustrates such a drug delivery device having an annular shape which does not completely encircle the entire cervix. FIG. 13 is the representation of FIG. 4 showing placement of a seventh embodiment of a tampon device 80 incorporating a scoop-shaped porous foam section 85. FIG. 14 is a side view of the tampon device 80 and FIG. 15 is a front view of the tampon device 80. The scoop-shaped porous foam section 85 is annular in shape, but does not completely encircle the cervix 5. Instead, the scoop-shaped porous foam section has a nib-shaped tip 81 which is designed to wedge itself into the posterior fornix 20. The scoop-shaped porous foam section 85 is designed to deliver medication to the vaginal wall along the entire length of the scoop-shaped porous foam section 85.

FIG. 16 is a cross-sectional representation of the vaginal area adjacent the cervix 5 with an eighth embodiment of a tampon drug delivery system according to the invention. In FIG. 16, the tampon device 82 comprises an absorbent tampon 84. The section 86 of the tampon 84 which rests against the cervix 5 contains high concentrations of medication. As the fibers absorb fluid, the tampon 84 expands around the cervix 5 and delivers medication to the tissue. The discharge will be drawn to proximal sections of the tampon 84 as fibers become more absorbent in this area. The tampon device 82 includes a string 88 for removal of the tampon device 82.

Suitable cylindrical cartridge containers or inserter tubes which assist in the insertion and storage of the tampon systems of the present invention will be apparent to those skilled in the art of tampon construction. Examples are described in U.S. Pat. Nos. 4,3178,447; 3,884,233; and 3,902,493.

In general practice, a drug delivery tampon device as described herein is placed into the vagina and the inserted tube is removed. The tampon device contacts the inner wall of the vagina and the penetration enhancer and mucoadhesive act to facilitate the absorption of the drug into the local vasculature. This results in a higher concentration of the drug being delivered to the systemic circulation.

Figure 17:
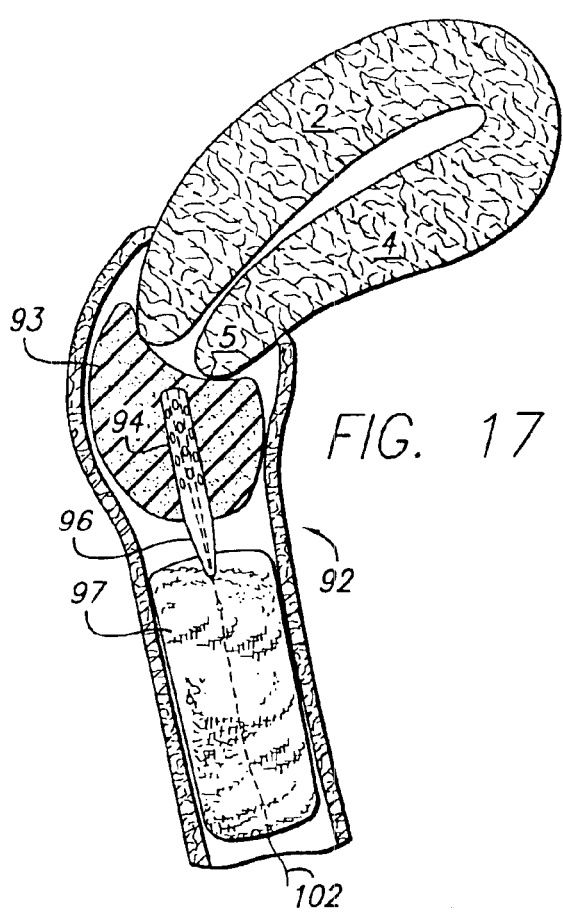
FIG. 17 is the representation of FIG. 4 showing placement of a tampon for drug delivery incorporating non-absorbent tubing comprising a distal opening.
Figure 18:
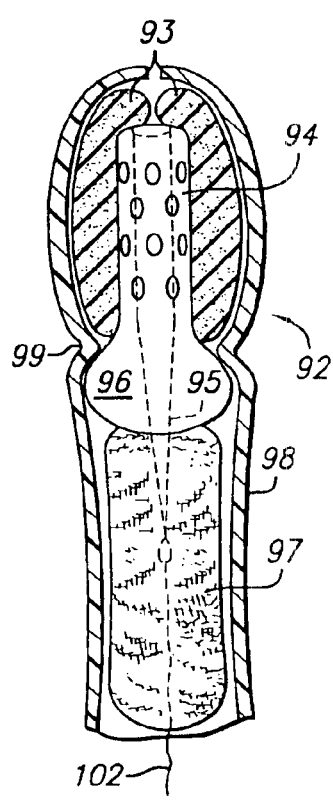
FIG. 18 is the tampon drug delivery system of FIG. 17 in a dehydrated, sheathed, state.
Figure 19:
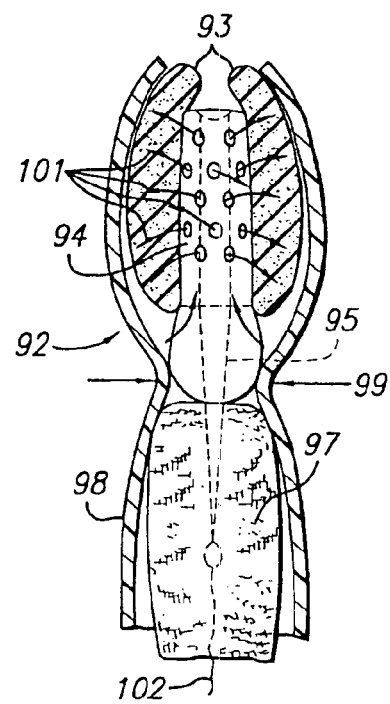
FIG. 19 is the tampon drug delivery system of FIG. 18 illustrating deployment of the tampon.

FIG. 17 is a cross-sectional representation of the vaginal area adjacent the cervix 5 with a ninth embodiment of a tampon drug delivery system according to the invention. In FIG. 17, the tampon device 92 includes a distal porous foam section 93 which, in its dehydrated, sheathed state (FIG. 18), is tight around a perforated outer tube 94. The perforated outer tube 94 is connected to a bladder 96 located proximally which is filled with liquid medication (not illustrated). Within the perforated outer tube 94 is a concentric inner tube 95 which provides a pathway for discharge to flow into an absorbent tampon 97 which is proximal to the porous foam section 93. Prior to insertion, the tampon device 92 is enveloped in a sheath 98 which is necked down 99 between the porous foam section 93 and the bladder 96 50 that, when the tampon device 92 is deployed and the sheath 98 moves over the bladder 96, the medication is forced out 101 through the perforated outer tube 94 into the porous foam section 93 (FIG. 19). The tampon device 92 includes a string 102 for removal of the tampon device 92.

Another example of a suitable controlled release drug delivery system for the present invention is the vaginal ring. Vaginal rings usually consist of an inert elastomer ring coated by another layer of elastomer containing bisphosphonate to be delivered. The rings can be easily inserted, left in place for the desired period of time (e.g., up to 7 days), then removed by the user. The ring can optionally include a third, outer, rate-controlling elastomer layer which contains no drug. Optionally, the third ring can contain a second drug for a dual release ring. The drug can be incorporated into polyethylene glycol throughout the silicone elastomer ring to act as a reservoir for drug to be delivered.

Pessaries, tablets and suppositories are other examples of drug delivery systems which can be used in the present invention. These systems have been used for delivery of vaginal medications and steroids, and have been described extensively in the literature.

Another example of a delivery system is the vaginal sponge. The desired bisphosphonate can be incorporated into a silicone matrix which is coated onto a cylindrical drug-free polyurethane vaginal sponge, as described in the literature.

Bioadhesive tablets are another drug delivery system. These bioadhesive systems use hydroxypropyl methylcellulose and polyacrylic acid. They release bisphosphonate for up to five days once they are placed in the appropriate formulation.

III. Treatment of Osteoporosis Paget's Disease and Related Bone Skeletal Diseases A method for treatment of osteoporosis, Paget's disease, bone and skeletal disease is based on the concept that the upper vagina is amply supplied with blood vessels connected to general circulation to permit preferential delivery of biphophonates via the transmucosal delivery to the circulation. This permits the higher concentrations of bisphosphonates to be delivered into circulation and to the bones than can be accomplished by oral administration.

Additionally, the treatment for osteoporosis or other diseases, as discussed below, may further comprise administration of an improved formulation which in addition to the bisphosphonate contains an estrogen, or in alternative the estrogen may be administered systemically in conjunction with the vaginal bisphosphonate treatment. In another alternative, the device may contain the exothermic portion or electrical stimulating device for release of the drug from the device.

The direct delivery of bisphosphonates according to the invention using the improved formulation results in much higher systemic bioavailability of the bisphosphonate without accompanying undesirable adverse reactions.

The concept of transmucosal vaginal delivery to the blood has been confirmed in the rabbit model utilizing two transmucosal vaginal formulations. The rabbit is the classic model for studying transmucosal drug delivery in the vagina and extrapolations to people have generally be applicable.

The most specific demonstration of the concept has been achieved with the drug alendronate, as described in Example 3.

A. Treatment of Osteoporosis

The major effect of currently available antiresorptive therapy for osteoporosis is to slow or arrest bone loss. Although antiresorptive therapies demonstrate increases in bone mineral density, the effect is usually transient, and a plateau in bone mineral density usually emerges at one year. When the treatment with the alendronate is continued, a steady improvement in bone mineral density occurs in years 2 and 3.

B. Treatment of Postmenopausal Osteoporosis

Osteoporosis is a disorder of skeletal fragility characterized by an imbalance in bone turnover such that bone resorption exceeds bone formation. Accelerated bone resorption is the principal physiological derangement responsible for both postmenopausal and age-related bone loss. Furthermore, increased bone turnover is itself a risk factor for fracture, independent of bone mineral density. Recent studies with etidronate, pamidronate, and alendronate demonstrate the ability of these drugs to suppress bone turnover and to preserve or increase bone mass. Both in large studies with alendronate and in long-term studies with clodronate in patients at high fracture risk treated with etidronate, decreased fracture occurrence was observed. Except for upper gastrointestinal intolerance with aminobisphosphonates, these drugs are very well tolerated.

Bisphosphonates are promising alternative to estrogen for the treatment of patients with decreased bone mass and, particularly, those with severe osteoporosis.

C. Treatment of Paget's Disease

Paget's disease of bone is a localized, monostotic or polyostotic disease characterized by increased bone remodeling, bone hypertrophy, and abnormal bone structure that in symptomatic patients leads to pain and bone deformity. Complications involve the bone fractures, neoplastic degeneration, or osteoarthritis of joints. The short-term objective of treatment is to alleviate bone pain, and the long-term objective is to minimize or prevent the progression of the disease.

Bisphosphonates, such as alendronate and pamidronate are used, in patients successfully treated with bisphosphonates, the new bone forms during treatment which bone appears to be lamellar rather than woven in structure. This histologic change is accompanied by major clinical, biochemical, and radiographic signs of improvement in the patient. With new bisphosphonate drugs, the suppression of disease activity is now attainable.

D. Metastases From Breast Cancer

Clinical research over the last decade has confirmed the helpful role of bisphosphonates in the management of patients with bone metastases secondary to breast cancer and other malignancies as well as in nonmetastatic bone cancer disease. This role is also expanding in myeloma. Current clinical research in oncology is focusing on their potential for the prevention of skeletal complications of malignant disease and the development of bone metastases while basic researchers are developing compounds of higher potency and, perhaps, higher therapeutic efficacy.

One of the earliest bisphosphonates investigated, etidronate, was found effective in the management of malignant hypercalcemia and, when used orally and intermittently, its administration results in reduced bone loss in osteoporosis.

Clodronate has been shown to be an effective agent in the management of hypercalcemia and can be used as a single intravenous administration for this purpose. Clodronate is also effective in some patients in reducing bone pain and improving mobility. When used orally, it can, as can pamidronate, reduce the skeletal complications of breast cancer such as hypercalcemia, bone fractures and bone pain. It may have fewer gastrointestinal side effects than oral pamidronate. There is emerging evidence that bisphosphonates may delay or prevent the clinical appearance of bone metastases as well as reduce other skeletal complications.

E. General Method for Transmucosal Vaginal Treatment with Bisphosphonate

In general, the method of the invention comprises vaginal administration of an improved formulation or insertion of a device comprising the improved formulation containing a bisphosphonate selected from the group consisting of alendronate, risedronate, clodronate, pamidronate, etidronate, tiludronate, neridronate, ibandronate olpadronate and incadronate for treatment of osteoporosis combined with a suitable delivery device or system which permits the transmucosal vaginal delivery through the vaginal mucosa of the drug to the blood circulation and bones.

The systems and methods of the invention provide several advantages over oral administration of drugs.

First, there is an increased concentration of drug delivered to the circulation due to the improved formulation. This provides for higher blood bioavailability of the drug by transmucosal delivery when compared to oral administration, as described above. Second, there is no effect of food on the absorption of the bisphosphonate, which reduces inter-individual variability in absorption.

Second, there is reduction of metabolism in the liver by avoiding the gastrointestinal system.

Third, the invention provides a continuous drug depot which allows continuous and uninterrupted delivery of drug over an extended period of time.

Fourth, and very important, is the reduction of side effects, particularly irritation and inflamation of esophagus and stomach mucosa. For example, the well established gastrointestinal side-effects of observed with oral administration of bisphosphonates do not arise with transmucosal administration, in the same way as with oral administration, as described herein.

Other features of the invention will become apparent in the course of the following descriptions of exemplary embodiments which are given for illustration of the invention and are not intended to be limiting thereof.

Utility

The present oral route for administering the bisphosphonates provides inadequate bioavailability of the active pharmaceutical agent and/or results in unacceptable side effects of gastrointestinal toxicity. The inhibition of their absorption by food makes dosing extremely inconvenient.

The method of transmucosal vaginal delivery of bisphosphonates and the improved formulations described herein, when applied to the vaginal mucosa, are able to deliver approximately 65–67% of the amount of bisphosphonates delivered intravenously and 65 to 67 times of the amount of bisphosphonates delivered orally. Moreover, it is at least twice as efficient as the previously disclosed transvaginal formulation.

EXAMPLE 1

Preparation of Alendronate Vaginal Suppository

This example describes the process for preparation of transvaginal suppositories for use in rabbits.

The dose of alendronate (Reddy Cheminor, India) was 0.15 mg/kg body weight. Radioactively labeled alendronate (4–7 $\mu$Ci) $^{14}$C was added to the unlabeled compound.

Vaginal suppositories were formulated and prepared 24 hours prior to each experiment. The three basic components of the formulation for preparation of suppositories were a lipophilic carrier SUPPOCIRE® AS2 (Gattefosse, Westwood, N.J.) (69% wt); a mucoadhesive agent hydroxypropyl methylcellulose (HPMC), obtained as METHOCEL® K, HPMC K15M, from Dow Chemical, Midland, Mich, (1.5% wt); and a penetration enhancer TRANSCUTOL® also obtained from Gattefosse (15% wt).

To make 10 suppositories for this rabbit studies, 2760 mg of SUPPOCIRE, 60 mg of HPMC, 600 mg of TRANSCUTOL, the calculated dose of the drug, and its labeled counterpart were weighed out. SUPPOCIRE was melted in a disposable 100 mL polypropylene beaker suspended in water at 50° C. The solution was stirred until completely melted. HPMC and TRANSCUTOL were then added and mixed. Finally, the unlabeled drug and the radioactively-labeled drug were added to the warm solution. The warm mixture was quickly poured into TYGON® tubing molds available from Fisher Scientific, Pittsburgh, Pa. (2 cm lengths). The tubing was kept upright on an ice-cold glass slab. Suppositories were kept refrigerated until use. The suppository was weighed prior to each experiment to determine and confirm the actual drug dose.

The quantitative composition of alendronate suppository used for these rabbit studies is as follows: 0.6 mg alendronate sodium (0.16 wt %), 276 mg SUPPOCIRE (69 wt %), 60 mg TRANSCUTOL (15 wt %), 6 mg HPMC (1.5 wt %), and 57.4 mg water (14.3 wt %).

EXAMPLE 2

Preparation of Pamidronate Vaginal Suppository

This example describes preparation of pamidronate-containing transvaginal suppositories for use in rabbits.

$^{14}$C-Pamidronate is commercially obtained from Amersham Life Science, Arlington Hts., Ill. The dose of unlabeled pamidronate (CN Biosciences) was 0.2 mg/kg body weight. All the other steps in the preparation of the pamidronate suppositories are identical to those of Example 1 with pamidronate replacing alendronate.

Suppositories comprising other bisphosphonates are prepared in the same way except that the amount of the bisphosphonate may vary.

EXAMPLE 3

Alendronate Pharmacokinetic Studies

This example describes procedures used for pharmacokinetic studies for alendronate transvaginal delivery in rabbits comparing an improved formulation of the invention with a previously described transmucosal vaginal formulation.

$^{4}$C-Alendronate was obtained from DuPont/NEN, Boston, Mass. Prior to intravenous injection, unlabeled alendronate (0.15 mg/kg body weight, i.v.) was dissolved in 0.5 mL saline. Labeled alendronate (4–7 pCi) was then added to the cold compound just prior to i.v. injection.

Female white New Zealand rabbits weighing 2.8 to 3.5 kg were obtained from Myrtle Rabbitry (Thompson Station, Tenn.) Rabbits were kept in a AALAC—approved facility and were acclimated to their environment at least 48 hours prior to each experiment.

Drug pharmacokinetic studies were performed via the intravenous, oral, and transvaginal modes of administration. During the first series of experiments, the intravenous route of administration was utilized to determine the alendronate pharmacokinetic parameters at 100% bioavailability. In the second series of experiments, the intravenous pharmacokinetic parameters were compared to corresponding values following oral and vaginal administration, respectively.

Briefly, after an 18 hour overnight fast, each rabbit was premedicated with ketamine (40 mg/kg, i.m.), xylazine (10 mg/kg, i.m.), and atropine (0.5 mg, i.m.). Rabbits used for oral administration were intubated and anesthesia was maintained with isoflurane (1–3%). Vital signs were monitored throughout the experiment via a pulse oximeter. Rabbit body temperature was kept constant by a recirculating heating pad. Intravenous access was achieved by placement of a 22 gauge TEFLON catheter in the peripheral ear vein. Intraarterial access was achieved by placement of a 22 gauge TEFLON catheter in the central artery in the ear. A heat lamp was used to warm the ears to promote peripheral blood flow.

After the rabbit was anesthetized, the mixture containing labeled and unlabeled drug was injected through the ear vein over a 10 second to 2 minute period. Blood samples were drawn through the arterial line at 0.1, 0.25, 0.5, 0.75, 2, 4, 6, 8, 10, 12 and 24 hours relative to the time of injection. Blood samples (1 mL) were placed in a polypropylene tube containing EDTA. The blood was centrifuged at 2000 rpm for 10 minutes and 0.5 mL of plasma was placed into a scintillation vial.

Solvable tissue solubilizer 0.5 mL (Packard, Meridian, Conn.) was added to the plasma samples and samples were vortexed for 30 seconds. 10 mL of Hionic-Fluor scintillation cocktail (Packard) was added and samples were vortexed for 1 minute before they were placed on the scintillation counter.

For the transmucosal vaginal experiments, vaginal suppositories were formulated and kept on ice. The suppository was introduced into the rabbit vagina using the barrel of a plastic transfer pipette (Baxter, McGaw Park, Ill.) and a tuberculin syringe as the plunger to load the suppository into the vagina to a depth of 7 to 8 cm. Blood samples were taken at 0.1, 0.25, 0.5, 0.75, 2, 4, 6, 8, 14, 20 and 25 hours relative to suppository administration.

Oral administrative of alendronate in anesthetized rabbits was achieved via gavage of a 2 ml drug solution in saline followed by 10 ml saline rinse. Blood samples were removed at 0.1, 0.2, 0.25, 0.5, 1.0, 1.5, 2.5, 3.5, 4.0, 6.0, 8.0, 12.0, 18.0 and 24 hours relative to the time of administration via gavage.

Alendronate in the amounts shown in Table 1 and FIGS. 1 and 2 was administered intravenously, transvaginally as described above, and orally. As shown in Table 1 above, maximum plasma levels of alendronate administered transvaginally were at least 22 times greater as those observed after oral administration and persisted for a prolonged period of time.

EXAMPLE 4

Preparation of a Gel Containing Alendronate for Transvaginal Application

This example describes the process for preparation of gel formulation for use in human patients.

250 mL of isotonic saline was heated to 80° C. and 7.5 grams of METHOCEL® and 75 grams of TRANSCUTOL® were added, with stirring. The resultant mixture was allowed to stand at room temperature for 2 hours. Then 120 mg of alendronate mixed together with 10 mg of Tween 80. The alendronate/Tween mixture and a quantity of isotonic saline sufficient to bring the total volume to 500 mL were added to the gel and thoroughly mixed.

The gel was incorporated into the transmucosal tampon.

EXAMPLE 5

Preparation of Pamidronate Containing Lotion for Transvaginal Application

This example describes the preparation of pamidronate-containing lotion for use in human patients.

Anhydrous pamidronate disodium (3 mg) is dissolved in one mL of sterile saline and added to one mL of JERGENS® standard fragrance free lotion. The mixture is stirred until pamidronate is equally distributed within the lotion.

EXAMPLE 6

Preparation of Clodronate Containing Gel for Transvaginal Application

This example describes the preparation of clodronate-containing gel preparations for use in human patients.

Clodronate (Sigma/Aldrich, St. Louis, Mo.) (200 mg) is added to one mL of gel comprised of the following ingredients: glycerin, mineral oil, polycarbophil, carbomer 934P, hydrogenated palm oil, glyceride, sodium hydroxide, sorbic acid, and purified water.

Resulting formulation was incorporated into a tampon-like device by soaking the device in the formulation.

EXAMPLE 7

Preparation of Bisphosphonate Containing Vaginal Suppositories

This example describes the preparation of bisphosphonate containing vaginal suppositories for use in human patients.

A vaginal suppository is prepared for human transmucosal administration of each one of the drugs alendronate, risedronate, clodronate, etidronate, pamidronate, tiludronate and neridronate at the indicated dose. All of the steps in the preparation of the drug suppository are identical to those of Example 1 except that no radiolabeled compound is used and the therapeutical amount of the drug for human use is incorporated.

The quantity of vaginal dosage form needed to deliver the desired dose will of course depend on the concentration of the active ingredient in the formulation. The therapeutic dosage range for vaginal administration of the formulations of the present invention will vary with the size of the patient and the degree of the affliction.

EXAMPLE 8

Preparation of Vaginal Medicated Tampons

This example describes the preparation of a medicated device of the invention.

Preparation of vaginal medicated tampons is essentially as described in Example 7. The drugs listed in Example 7 are added to the tampon materials as gels, creams, ointment, powders, solutions, suspension, emulsions or suppository either before the tampon is fabricated or the prefabricated tampons are soaked in the solution, suspension, emulsion or other fluid preparation. The amount of the drug is such that it assures that the dose administered by vaginal tampon is at least as high as the one indicated in Example 8 and is delivered transmucosally in a dose-linear manner, as much as possible.

EXAMPLE 9

Vaginal Ointment

This example describes preparation of vaginal ointment.

Vaginal ointment according to the invention comprises an oil and an aqueous phase.

| Oil Phase | Aqueous Phase |
| --- | --- |
| Hydroxypropyl methylcellulose | Water |
| Acetylated lanolin | Bisphosphonate |
| Mineral oil 70 | Preservative |
| Amerchol L-500 | Mucoadhesive |
| Amerchol CAB | |
| Microcrystalline wax | |
| Cetyl alcohol | |
| Brij 52 | |
| Brij 58 | |
| Carbopol | |

For preparation of the ointment the drug selected from the group of compounds consisting of alendronate, clodronate tiludronate, pamidronate, etidronate, ibandronate, neridronate, risedronate, incadronate, minodronate, zoledronic acid or olpadronate is dissolved in the aqueous phase and the oil phase added. Both phases are properly mixed.

EXAMPLE 10

Vaginal Cream

This example describes preparation of vaginal cream containing bisphosphonate.

Vaginal cream comprises phase A components and phase B components.

| Phase A | Phase B |
| --- | --- |
| Purified water | Carbopol |
| Borax | Light mineral oil |
| Methylparabe | Synthetic beeswax |
| Bisphosphonate | Glyceryl monostearate, pure |
| | Propylparaben |
| | Hydroxypropyl methylcellulose |

Methylparaben, borax and the bisphosphonate is dissolved in water. Propylparaben is dissolved in as well mixed mixture of Phase B. Phase B is added to phase A with rapid stirring.

EXAMPLE 11

Vaginal Powder

This example describes preparation of vaginal powder containing a bisphosphonate for incorporation into the device of the invention or for delivery by spraying.

Vaginal powder is prepared by dissolving hydroxypropyl methylcellulose in water with heat. The mixture is slightly cooled and the bisphosphonate is added. The mixture is lyophilized.

EXAMPLE 12

Vaginal Tablet

This example describes preparation of a vaginal tablet.

Tablet for vaginal delivery is manufactured either by wet granulation or direct compression.

The following components are used:

Microcrystalline hydroxypropyl methylcellulose
Anhydrous lactose
Crosscarmellose sodium
Magnesium stearate
Bisphosphonate

What is claimed is:

1. A method for a transmucosal delivery of bisphosphonates to a systemic circulation for treatment of osteoporosis and Paget's disease and for treatment of a metastatic bone disease in a human female patient, wherein a bisphosphonate is delivered into the systemic circulation through the vaginal mucosa from a vaginal device incorporated with a transmucosal vaginal composition, said method comprising steps of:

a) providing the transmucosal vaginal composition consisting essentially of from about 0.01 to about 3200 mg of the bisphosphonate selected from the group consisting of alendronate, clodronate, etidronate, pamidronate, tiludronate, ibandronate, neridronate, risedronate, zoledronic acid, incadronate, minodronate and olpadronate;

from about 40% to about 95% of a saturated mono-, di- or triglyceride of fatty acids from 8 to 18 carbons or a mixture thereof;

from about 0.01% to about 5% of a mucoadhesive agent selected from the group consisting of alginate, pectin and a cellulose derivative; and from about 5% to about 25% of ethoxydiglycol;

wherein said composition is formulated and incorporated into the device as a suppository, cream, spray, gel, film, powder, foam, ointment, microcapsules, nanocapsules or a capsule containing microparticles or nanoparticles;

b) incorporating said composition into said vaginal device wherein said vaginal device is a vaginal tampon, vaginal ring, vaginal strip, vaginal capsule, vaginal tablet, vaginal pessary, vaginal cup or vaginal sponge; and c) delivering said composition to the vaginal mucosa by inserting said device into the vagina.

2. The method of claim 1 wherein said composition contains daily dose from about 0.05 to about 40 mg of alendronate, from about 1 to about 3200 mg of clodronate, from about 0.05 to about 20 mg/kg of etidronate, from about 1 to about 3000 mg of pamidronate, from about 0.02 to about 400 mg of tiludronate, from about 0.01 to about 50 mg of ibandronate, from about 0.1 to about 150 mg of neridronate, or from about 0.05 to about 30 mg of risedronate, from about 60 to about 85% of the saturated triglyceride of fatty acids, from about 0.01 to about 5% of the mucoadhesive agent and from about 5 to about 20% of ethoxydiglycol.

3. The method of claim 2 wherein said mucoadhesive agent is hydroxypropyl methylcellulose.

4. The method of claim 3 wherein said composition is consisting essentially of about 1.5% of hydroxypropyl methylcellulose, about 69% of saturated triglyceride of fatty acids and about 15% of ethoxydiglycol.

5. The method of claim 4 wherein the bisphosphonate is released from said composition incorporated into said device in a controlled release manner.

6. A method for treatment osteoporosis and Paget's disease and for treatment of a metastatic bone disease in a human female patient by a transmucosal delivery of bisphosphonates to the systemic circulation wherein a bisphosphonate is delivered to, absorbed through and delivered into the systemic circulation across the vaginal mucosa from a transmucosal composition, said method comprising steps of:

a) providing the transmucosal vaginal composition containing daily doses from about 0.001 to about 3200 mg of the bisphosphonate selected from the group consisting of alendronate, clodronate, etidronate, pamidronate, tiludronate, ibandronate, neridronate, risedronate, zoledronic acid, incadronate, minodronate and olpadronate;

from about 40 to about 95% of a saturated mono-, di- or triglyceride of fatty acids from 8 to 18 carbons or a mixture thereof;

from about 0.01 to about 5% of hydroxypropyl methylcellulose; and from about 5 to about 25% of ethoxydiglycol;

wherein said composition is formulated as a suppository, cream, gel, foam, ointment, capsule, microcapsules, nanocapsules or a capsule containing microparticles or nanoparticles, and b) delivering said composition to the vaginal mucosa.

7. The method of claim 6 wherein said composition contains daily doses from about 0.05 to about 40 mg of alendronate, from about 1 to about 3200 mg of clodronate, from about 0.05 to about 20 mg/kg of etidronate, from about 1 to about 3000 mg of pamidronate, from about 0.02 to about 400 mg of tiludronate, from about 0.01 to about 50 mg of ibandronate, from about 0.1 to about 150 mg of neridronate, or from about 0.05 to about 30 mg of risedronate, from about 60 to about 85% of the monoglyceride, diglyceride or triglyceride of fatty acids, from about 0.5 to about 3% of hydroxypropyl methylcellulose and from about 10 to about 20% of ethoxydiglycol.

8. The method of claim 7 wherein said hydroxypropyl methylcellulose is present in about 1.5%.

9. The method of claim 8 wherein said composition is consisting essentially of about 1.5% of hydroxypropyl methylcellulose, about 69% of the triglyceride of the saturated fatty acids and about 15% of ethoxydiglycol.

10. The method of claim 9 wherein said composition further comprises from about 5 to about 25% of solubilizing agent.

11. The method of claim 10 wherein the composition is administered daily, bi-daily, weekly, monthly or quarterly.

12. The method of claim 11 wherein said composition is administered weekly, monthly, quarterly or at any other interval chosen for the therapeutic regimen of a defined bisphosphonate.

13. The method of claim 12 wherein said composition is incorporated into a vaginal tampon and delivered by releasing said composition from said tampon in a controlled release manner.

14. A transmucosal vaginal composition for vaginal delivery of bisphosphonates to a human female patient, said composition consisting essentially of:

about 0.05 to about 40 mg of alendronate, about 1 to about 3200 mg of clodronate, about 0.05 to about 20 mg/kg of etidronate, about 1 to about 3000 mg of pamidronate, about 0.02 to about 400 mg of tiludronate, about 0.01 to about 50 mg of ibandronate, about 0.01 to about 150 mg of neridronate, and about 0.05 to about 30 mg of risedronate, formulated in admixture with about 0.5–5% of hydroxypropyl methylcellulose, about 90–95% of saturated monoglyceride, diglyceride, or triglyceride of fatty acids, and about 15% of ethoxydiglycol.

15. The composition of claim 14 wherein said bisphosphonate is alendronate formulated in the range of daily doses from about 0.05 mg to about 40 mg for administration as a daily, weekly or monthly dose.

16. The composition of claim 14 wherein said bisphosphonate is pamidronate formulated in the range of daily doses from about 1 mg to about 3000 mg for administration as a daily, weekly or monthly dose.

17. The composition of claim 16 wherein said bisphosphonate is clodronate formulated in the range of daily doses from about 1 to about 3200 mg for administration as a daily, weekly or monthly dose.

18. The composition of claim 14 wherein said bisphosphonate is etidronate formulated in the range of daily doses from about 0.05 to about 20 mg/kg for administration as a daily, weekly dose or monthly dose.

19. The composition of claim 14 wherein said bisphosphonate is tiludronate formulated in the range of daily doses from about 0.02 mg to about 400 for administration as a daily, weekly or monthly dose.

20. The composition of claim 14 wherein said bisphosphonate is neridronate formulated in the range of daily doses from about 0.1 mg to about 150 mg for administration as a daily, weekly or monthly dose.

21. The composition of claim 14 wherein said bisphosphonate is risedronate formulated in the range of daily doses from about 0.05 mg to about 30 mg for administration as a daily, weekly dose or monthly dose.

22. The composition of claim 14 wherein said bisphosphonate is ibandronate formulated in the range of daily doses from about 0.01 mg to about 50 mg for administration as a daily, weekly or monthly dose.

23. The composition of claim 14 additionally comprising an excipient selected from the group consisting of glycerin, polyoxyethylene sorbitan monooleate, mineral oil, polycarbophil, carbomer, hydrogenated palm oil, glyceride, sodium hydroxide and sorbic acids.

24. A medicated intravaginal device for a transmucosal delivery of bisphosphonates to the general circulation, wherein said device is a vaginal tampon, vaginal ring, vaginal strip, vaginal capsule, vaginal applicator, vaginal tablet, vaginal bioadhesive tablet, vaginal pessary, vaginal cup or vaginal sponge incorporated with a transmucosal composition consisting essentially of a bisphosphonate selected from the group consisting of 0.05 to about 40 mg of alendronate, about 1 to about 3000 mg of clodronate, about 0.05 to about 20 mg of etidronate, about 1 to about 3000 mg of pamidronate, about 0.02 to about 400 m of tiludronate, about 0.01 to about 50 mg of ibandronate, about 0.1 to about 150 mg of neridronate, and about 0.5 to about 30 mg of risedronate;

about 1.5% of hydroxypropyl methylcellulose;

about 69.5% of saturated triglyceride of fatty acids; and about 15% of ethoxydiglycol.

25. The device of claim 24 wherein said composition incorporated into said device is formulated as a suppository, cream, lotion, gel, ointment, film, foam, capsule, microcapsule, nanocapsule or a capsule containing microparticles or nanoparticles.

26. The device of claim 25 suitable for transmucosal delivery of the bisphosphonate for treatment of osteoporosis and Paget's disease or for treatment of a metastatic bone disease in a human female patient wherein said device is configured to make and maintain a contact with a vaginal mucosa or epithelium.

27. The device of claim 26 wherein said device is the vaginal tampon impregnated with the transmucosal composition containing at least one bisphosphonate.

* * * * *